(12) United States Patent
Khan

(10) Patent No.: US 8,560,339 B2
(45) Date of Patent: Oct. 15, 2013

(54) SYSTEM AND METHOD TO PREDICT THE GLOBAL SPREAD OF INFECTIOUS AGENTS VIA COMMERCIAL AIR TRAVEL

(75) Inventor: Kamran Khan, Toronto (CA)

(73) Assignee: Kamran Khan, Toronto (CA)

(*) Notice: Subject to any disclaimer, the term of this patent is extended or adjusted under 35 U.S.C. 154(b) by 763 days.

(21) Appl. No.: 12/593,976

(22) PCT Filed: Apr. 2, 2008

(86) PCT No.: PCT/CA2008/000617
§ 371 (c)(1),
(2), (4) Date: Sep. 30, 2009

(87) PCT Pub. No.: WO2008/119182
PCT Pub. Date: Oct. 9, 2008

(65) Prior Publication Data
US 2010/0042394 A1    Feb. 18, 2010

Related U.S. Application Data

(60) Provisional application No. 60/909,633, filed on Apr. 2, 2007.

(51) Int. Cl.
G06Q 10/00 (2012.01)
G06Q 10/10 (2012.01)
(52) U.S. Cl.
USPC .................................................. 705/2; 705/3
(58) Field of Classification Search
USPC ......................................................... 705/2, 3
See application file for complete search history.

(56) References Cited

U.S. PATENT DOCUMENTS

2004/0019574 A1    1/2004  Meng et al.
2008/0243584 A1*  10/2008  Srinivasan ........................ 705/9

FOREIGN PATENT DOCUMENTS

WO          88/04935 A1    7/1988

OTHER PUBLICATIONS http://www.nature.com/nature/journal/v429/n6988/pdf/nature02541.pdf.*
Lauren, A Meyers, Fighting Deadly Diseases"strategies for prediction and Contaiment" http://www.esi.utexas.edu/outreach/ols/lectures/ppts/42.pdf.*
Dr. Lauren Ancel Meyers, Fighting Deadly Diseases: "Strategies for predcition and Containment" Apr. 7, 2006 http://www.esi.utexas.edu/k-12-a-the-community/hot-science-cool-talks/lecture-archives.*

(Continued)

Primary Examiner — Dilek B Cobanoglu
Assistant Examiner — Maroun Kanaan
(74) Attorney, Agent, or Firm — McMillan LLP

(57) ABSTRACT

The invention comprises a system for predicting transmission of an infectious agent via air travel, comprising: a) a database, the database containing air passenger travel data for air travel between origin cities and destination cities, the air passenger travel data including: frequency of flights from origin cities to destination cities, number of passengers traveling from origin cities to destination cities, number of direct non-stop flights from origin cities to destination cities, total passenger traffic for origin and destination cities, and corresponding date stamps for all air passenger travel data; b) a modeling engine operative to map the air passenger travel data with the infectious agent to determine the probability of infection of an individual destination city from an individual origin city via air travel; and c) a reporting engine operative to produce a probability of infection of the individual destination city from the individual origin city at a given time based on said map.

27 Claims, 28 Drawing Sheets

(56) References Cited

OTHER PUBLICATIONS http://www.esi.utexas.edu/outreach/ols/lectures/ppts/42.pdf Lauren A. Meyers.*

Colizza et al.: "The modeling of Global Epidemics: Stochastic Dynamics and Predictability". Society for Mathematical Biology, vol. 68, Issue 8, pp. 1893-1921: published Jun. 20, 2006.

Colizza et al.: "Modeling the Worldwide Spread of Pandemic Influenza: Baseline Case and Containment Interventions", PloS Medicine, vol. 4, Issue 1, pp. 95-110; published Jan. 23, 2007.

Caley et al.: "The Waiting Time for Inter-Country Spread of Pandemic Influenza", PloS ONE, Issue 1, e 143, pp. 1-8; published: Jan. 3, 2007.

* cited by examiner

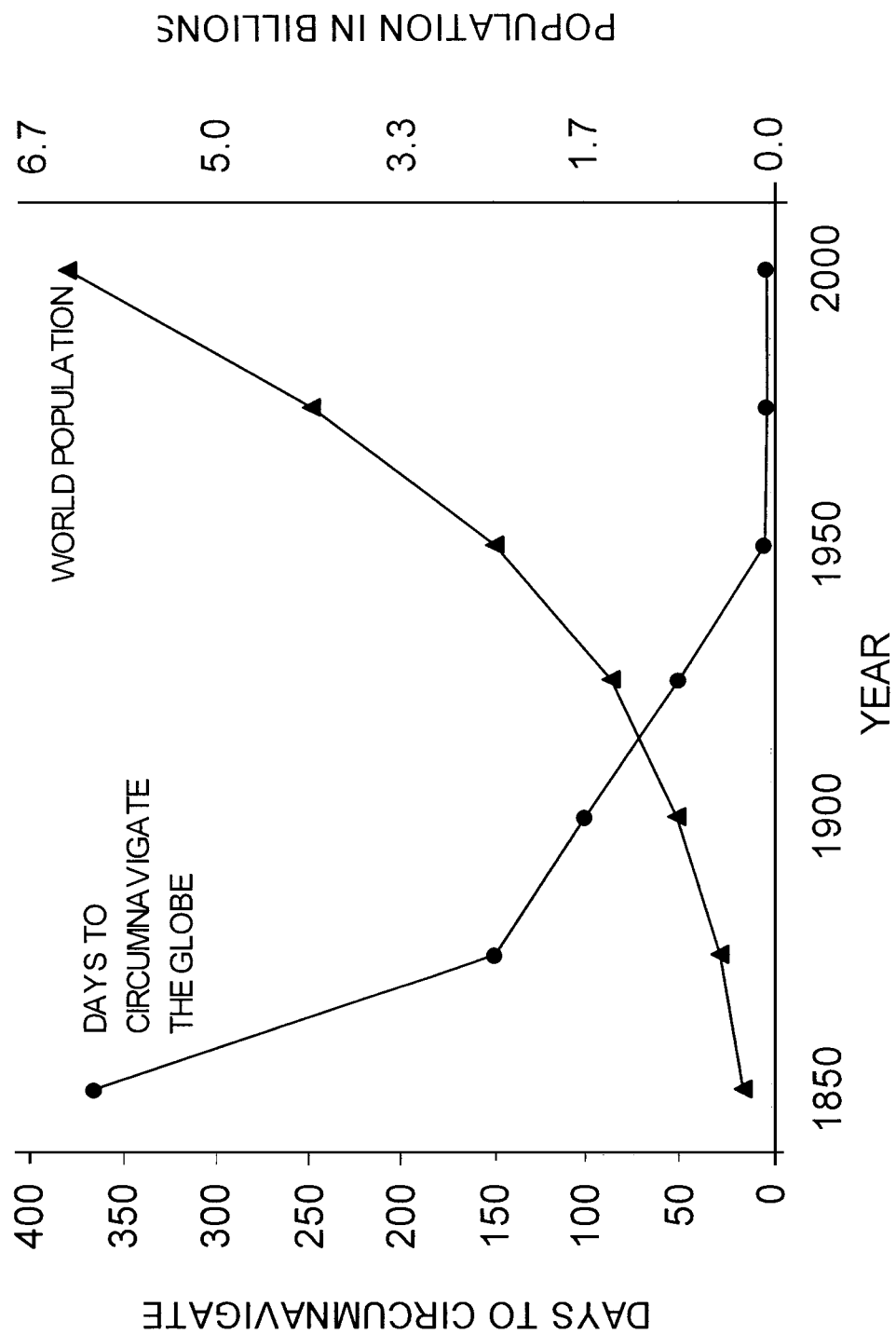
- FIGURE 1 -

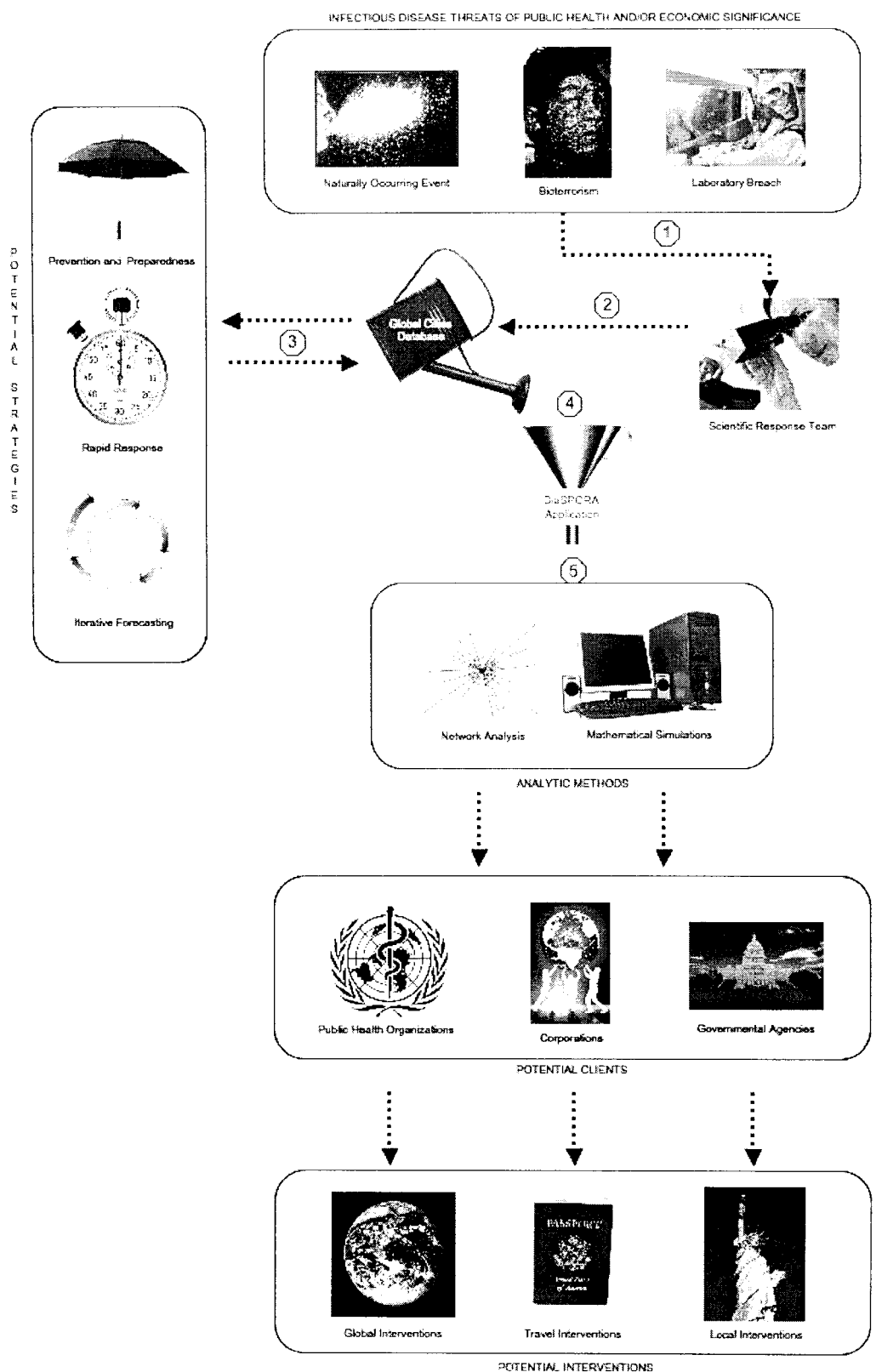
- FIGURE 2 -

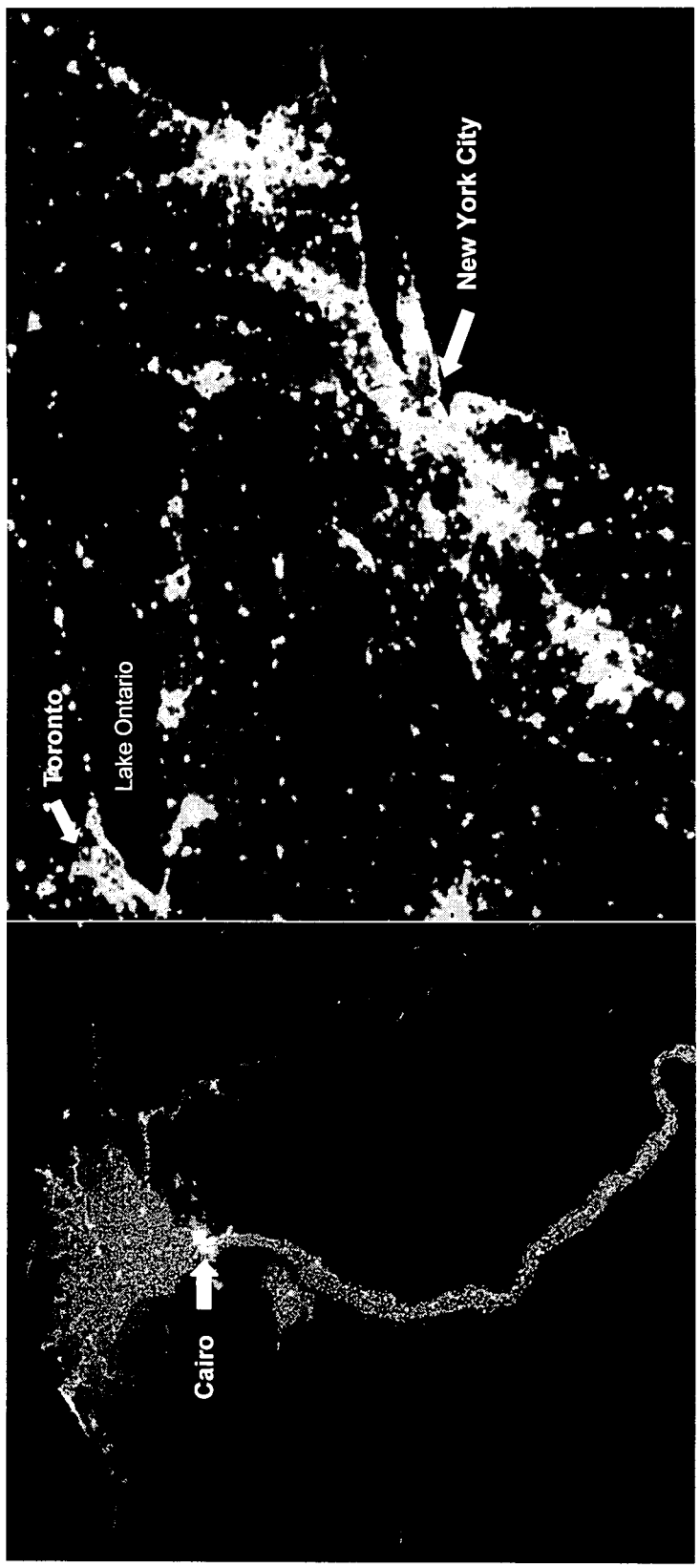
- FIGURE 3B -
- FIGURE 3A -

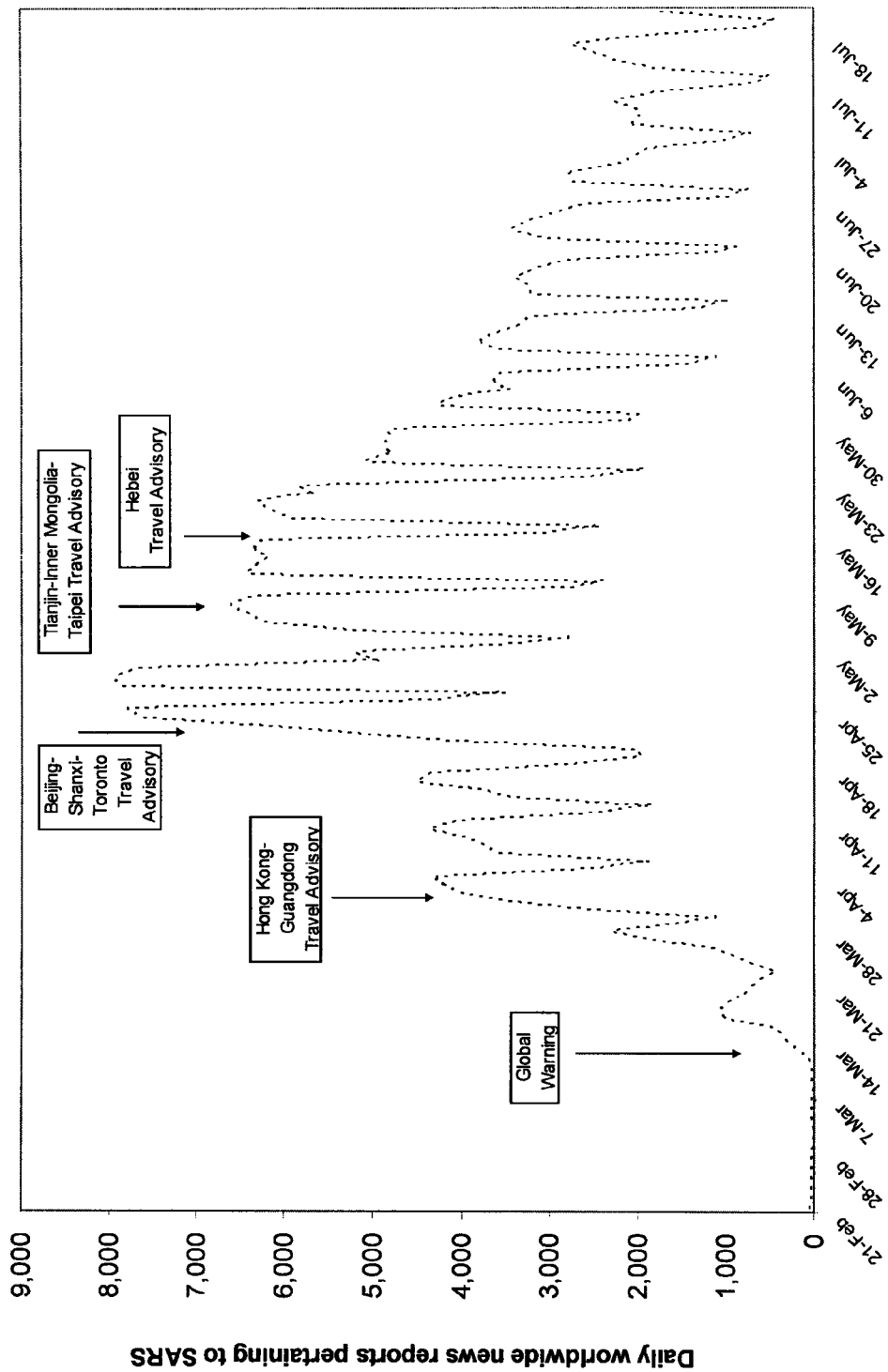
- FIGURE 4 -

- FIGURE 5 -

- FIGURE 6 -

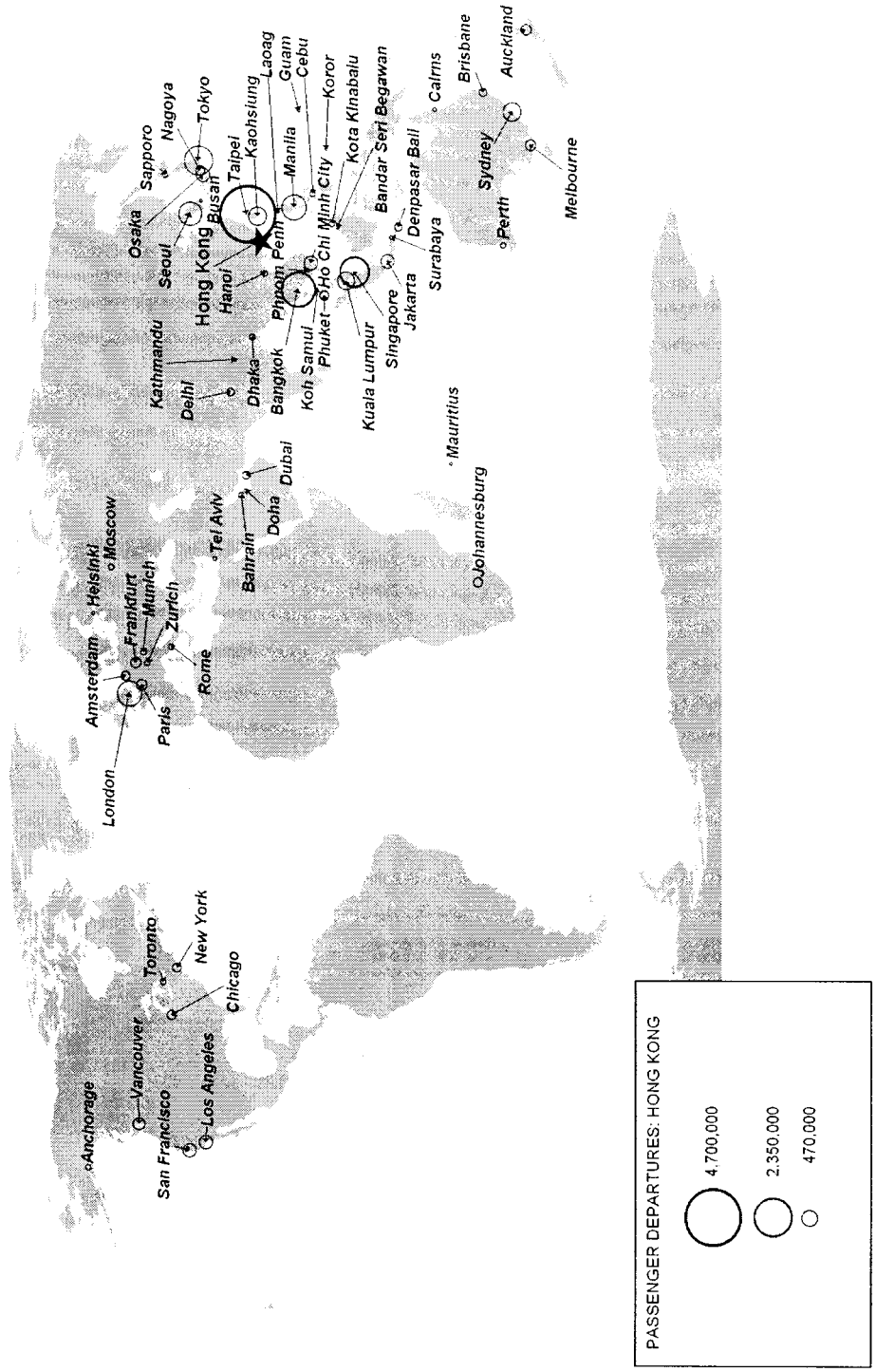
- FIGURE 7 -

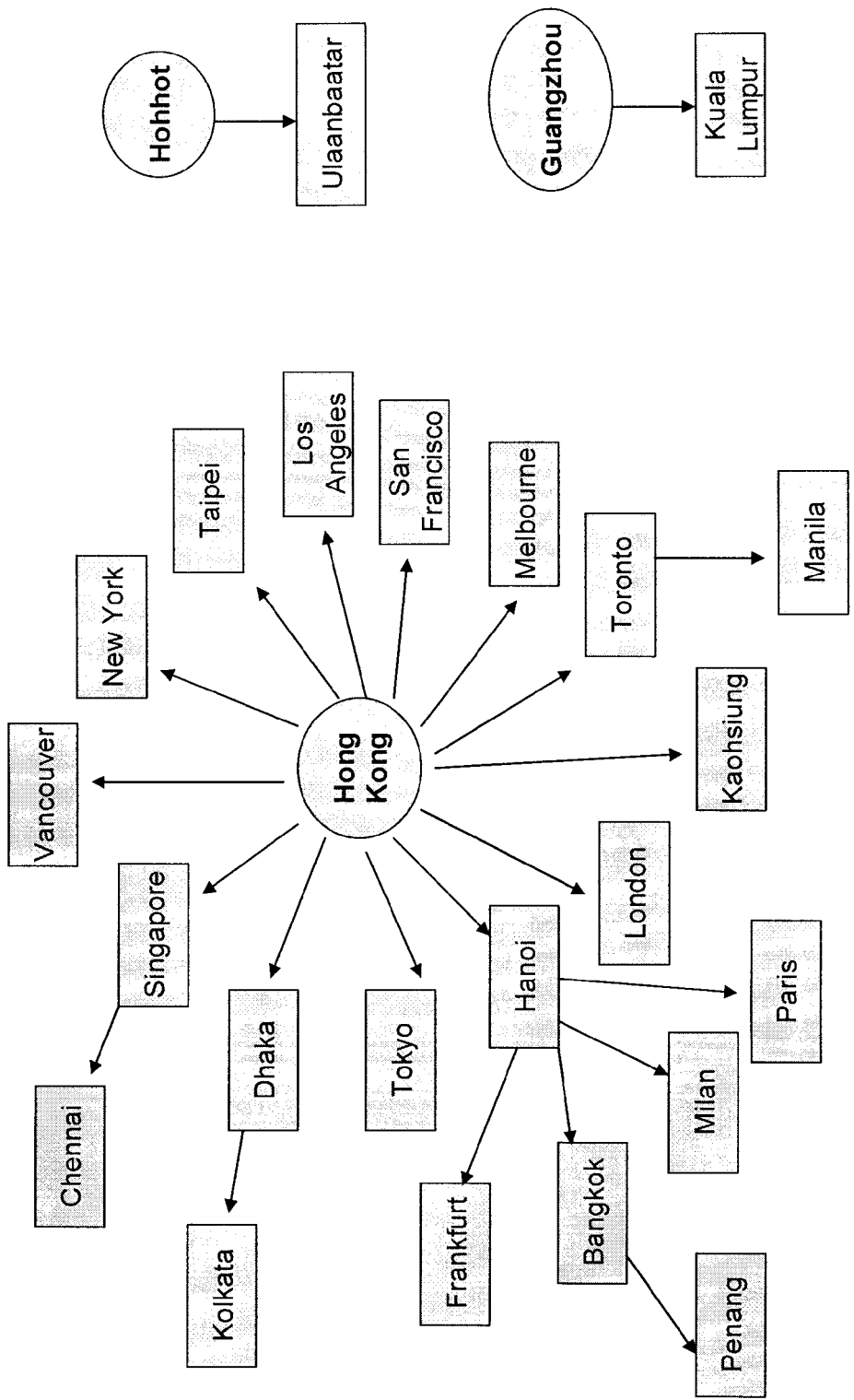
- FIGURE 8 -

- FIGURE 9 -

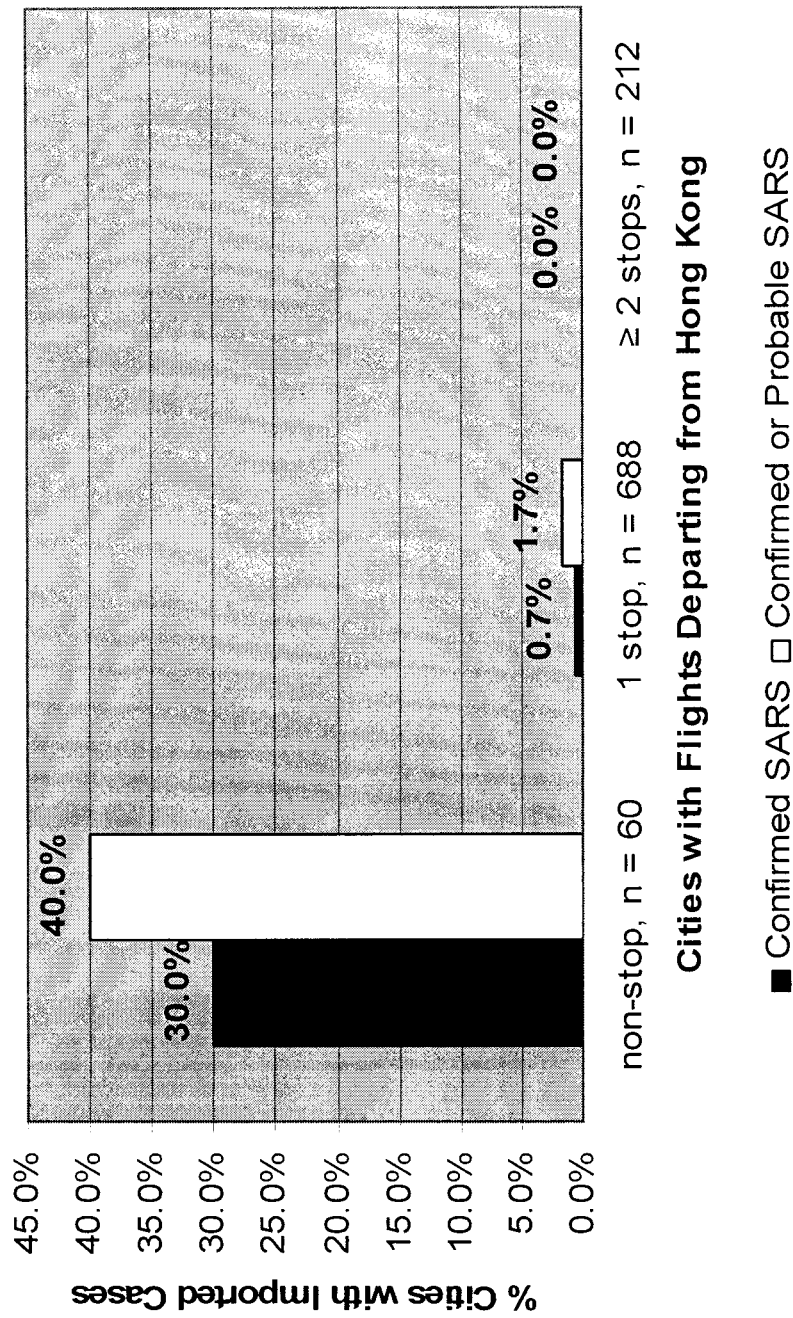
- FIGURE 10 -

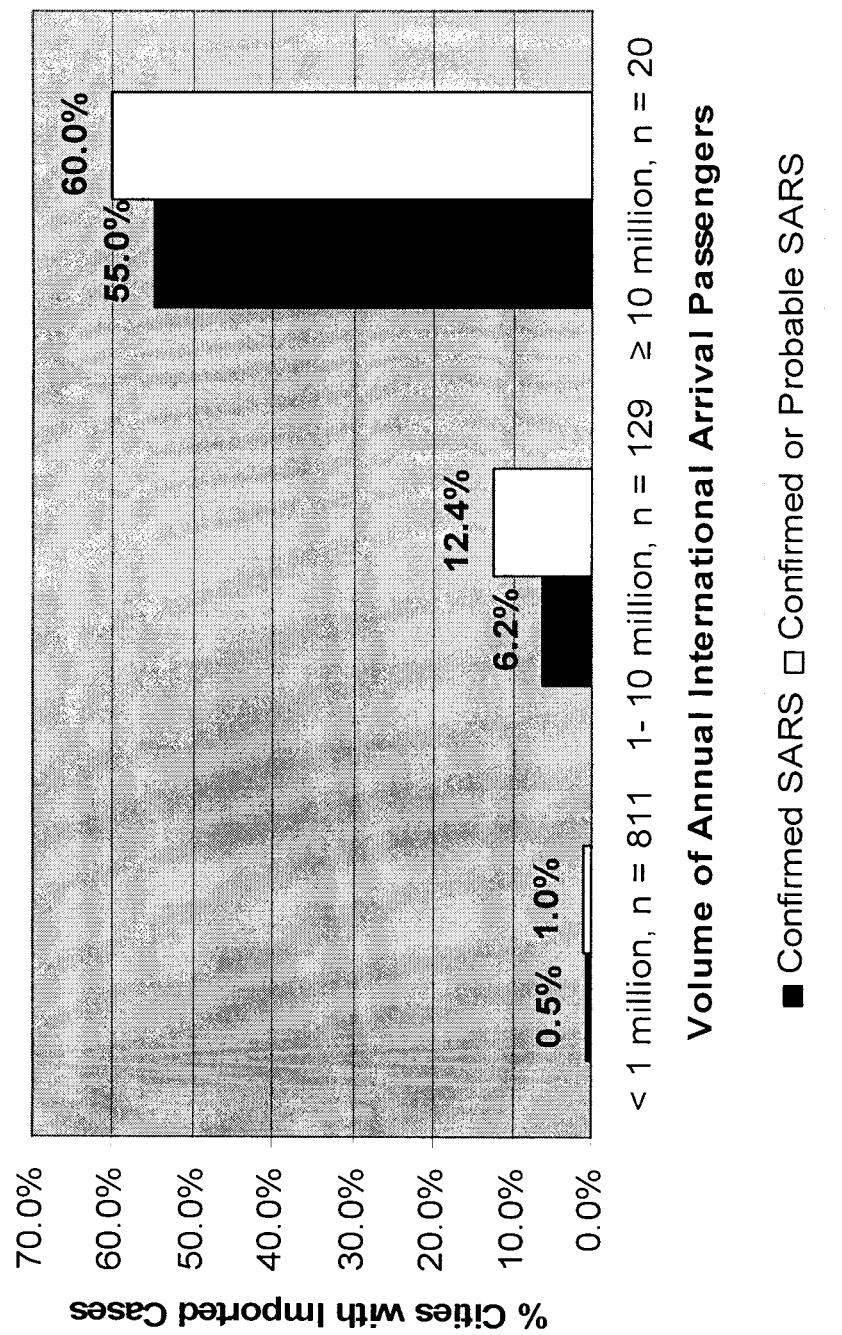
- FIGURE 11 -

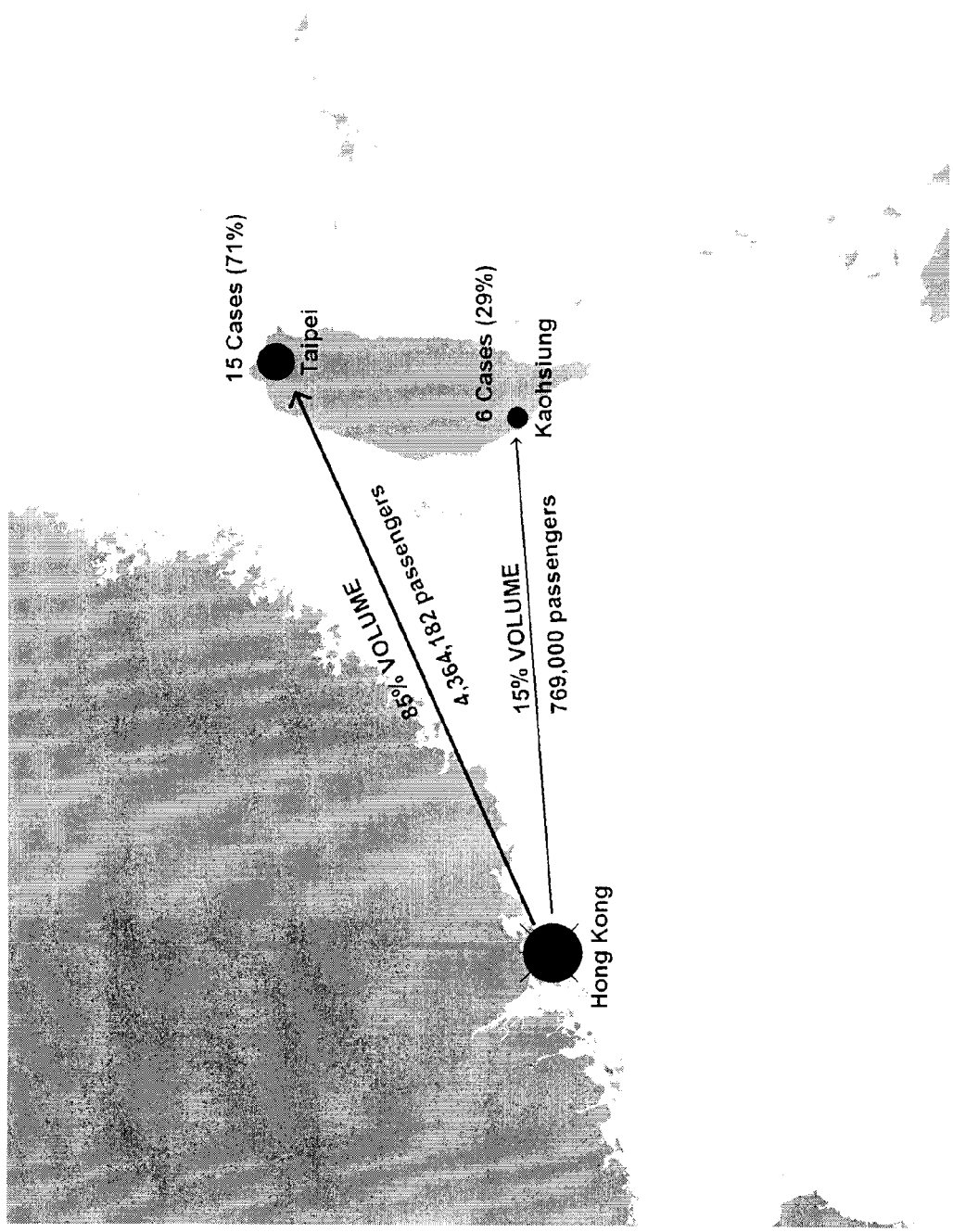
- FIGURE 12 -

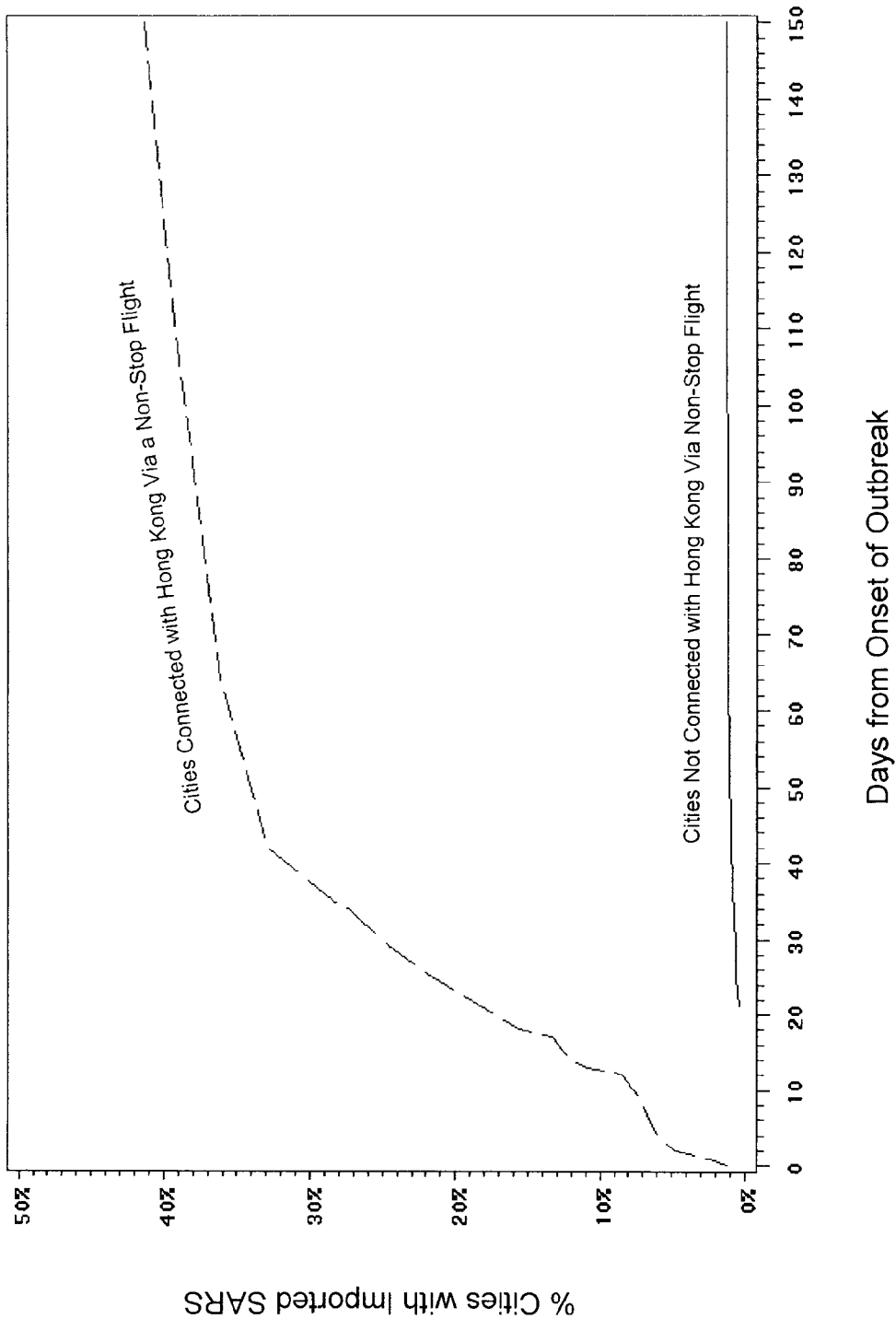
- FIGURE 13 -

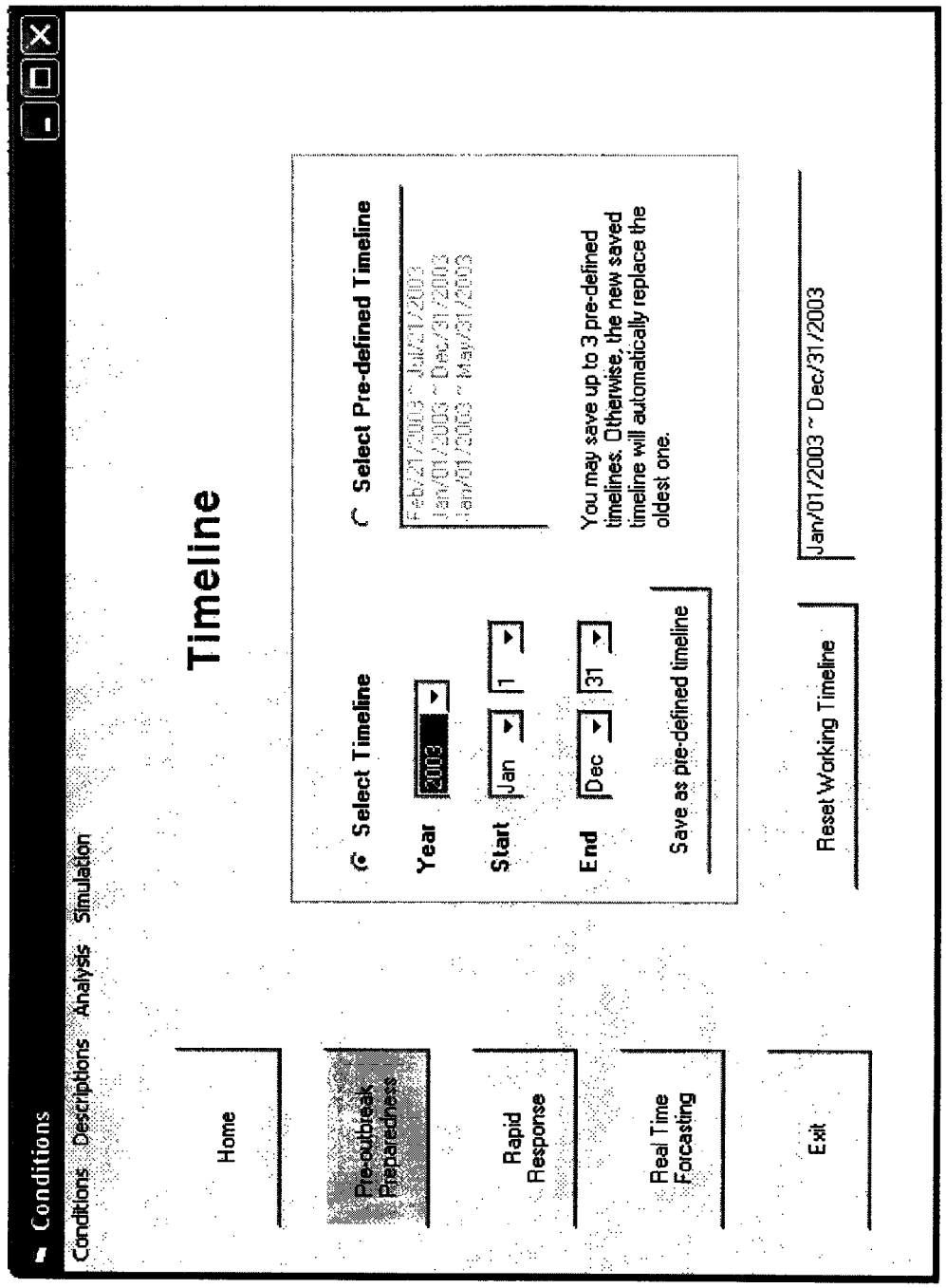
- FIGURE 14 -

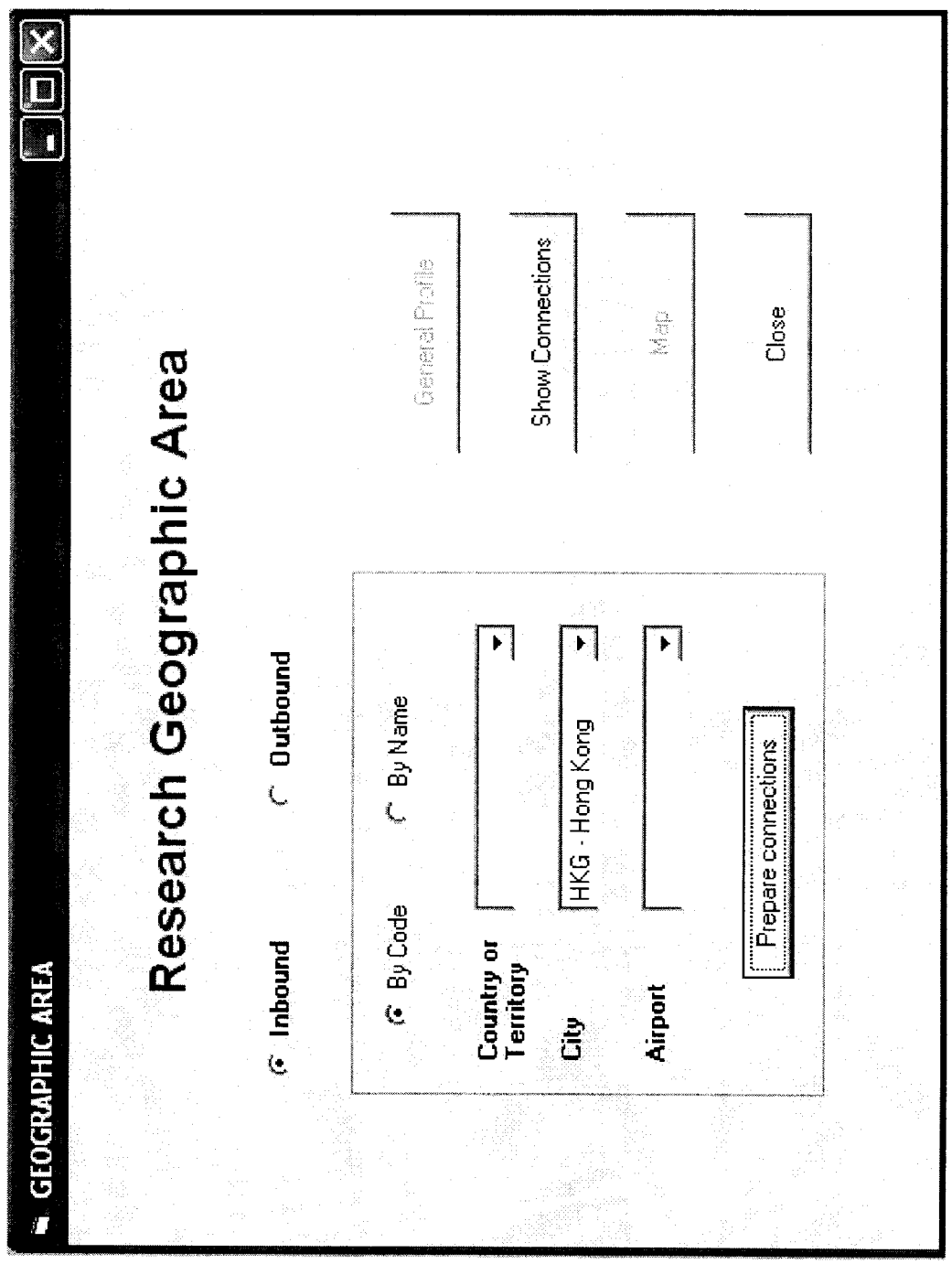
- FIGURE 15 -

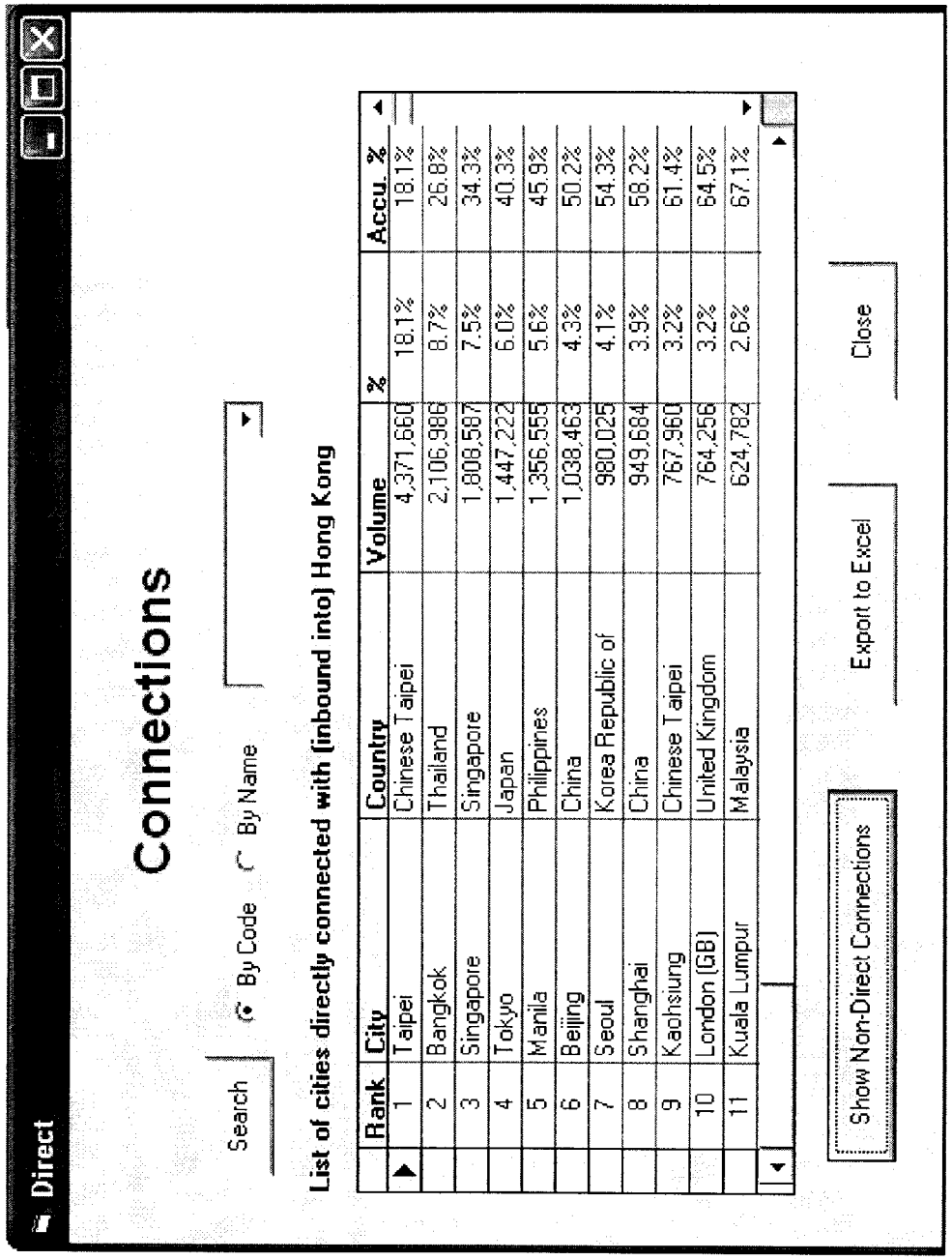
- FIGURE 16 -

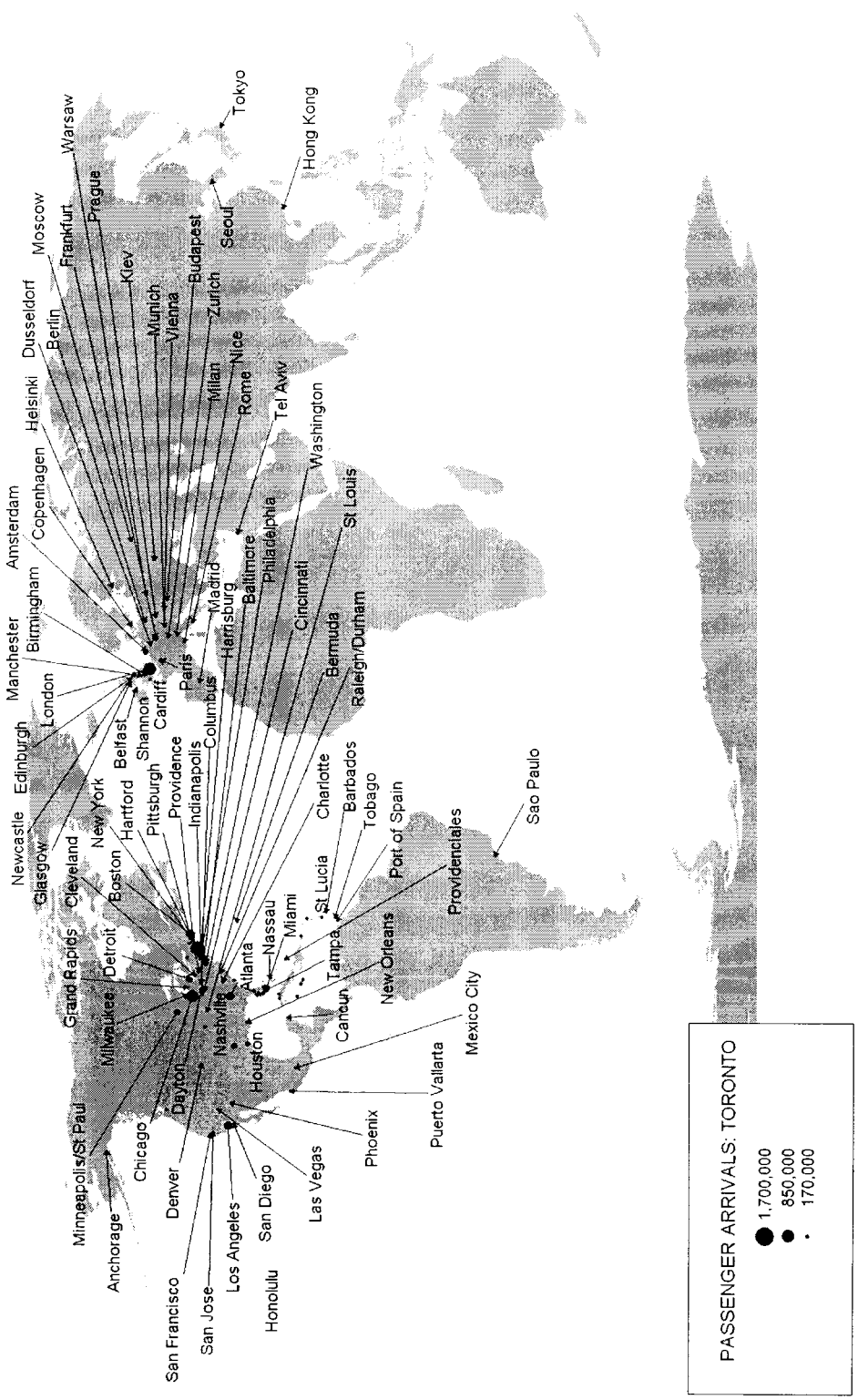
- FIGURE 17 -

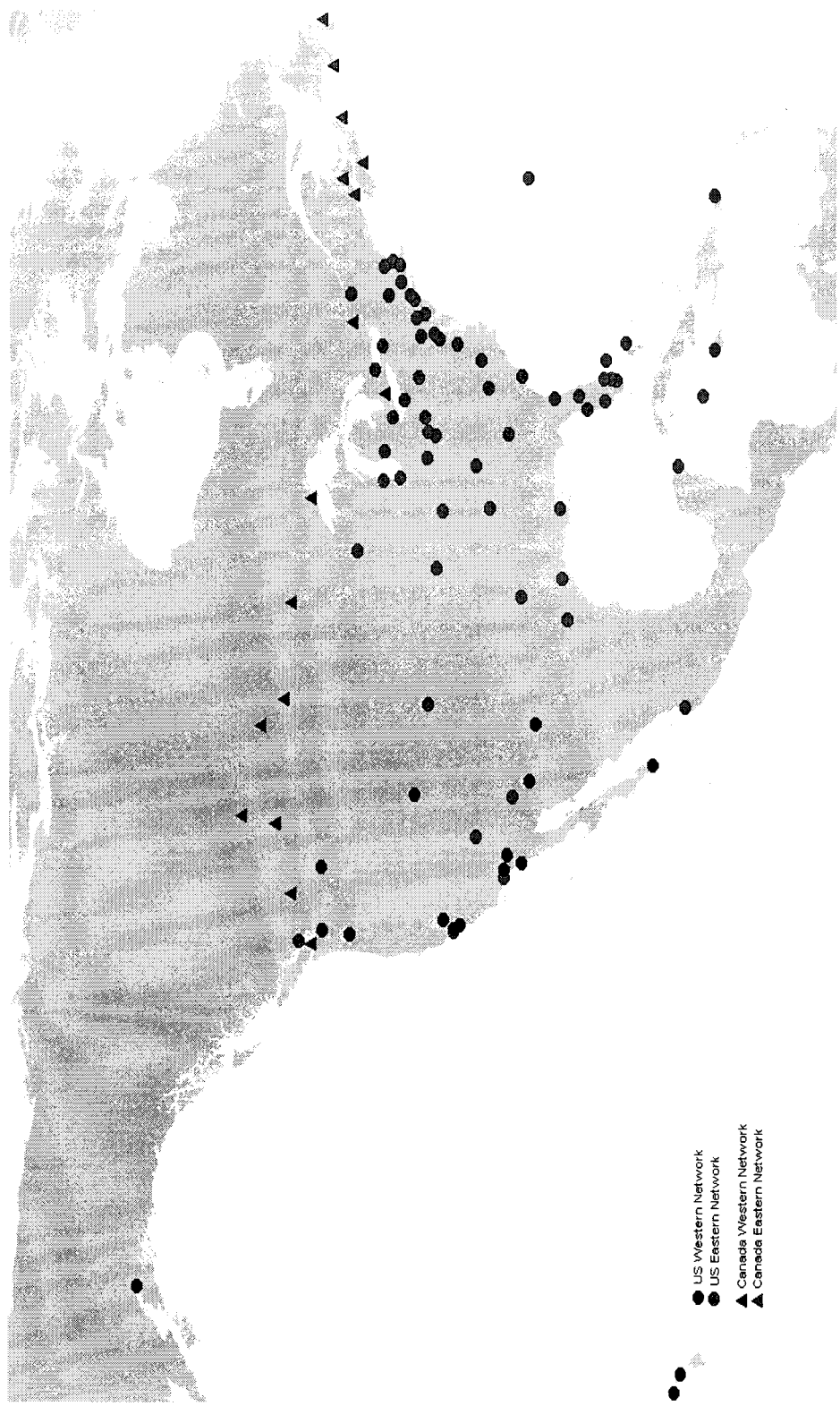
- FIGURE 18 -

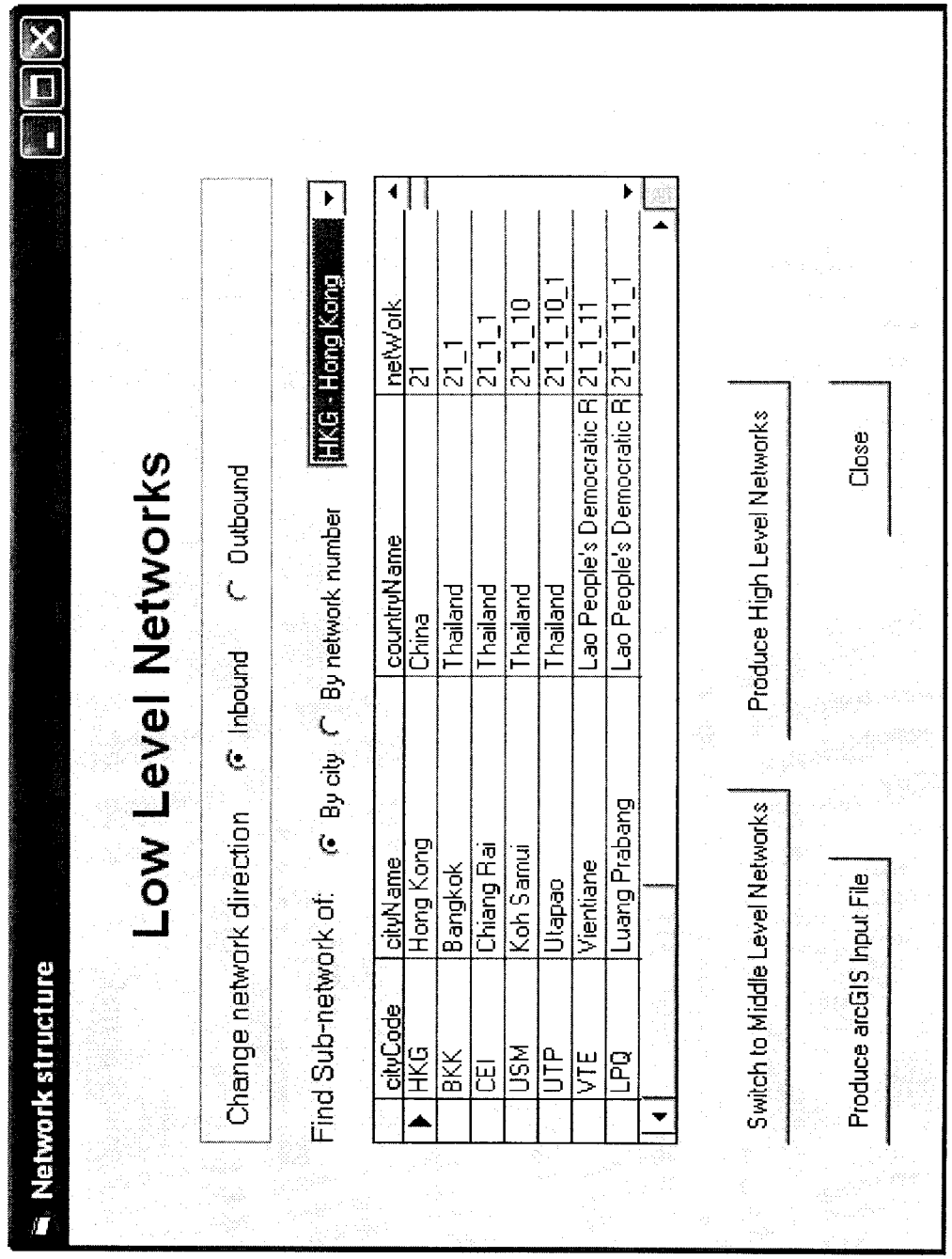
- FIGURE 19 -

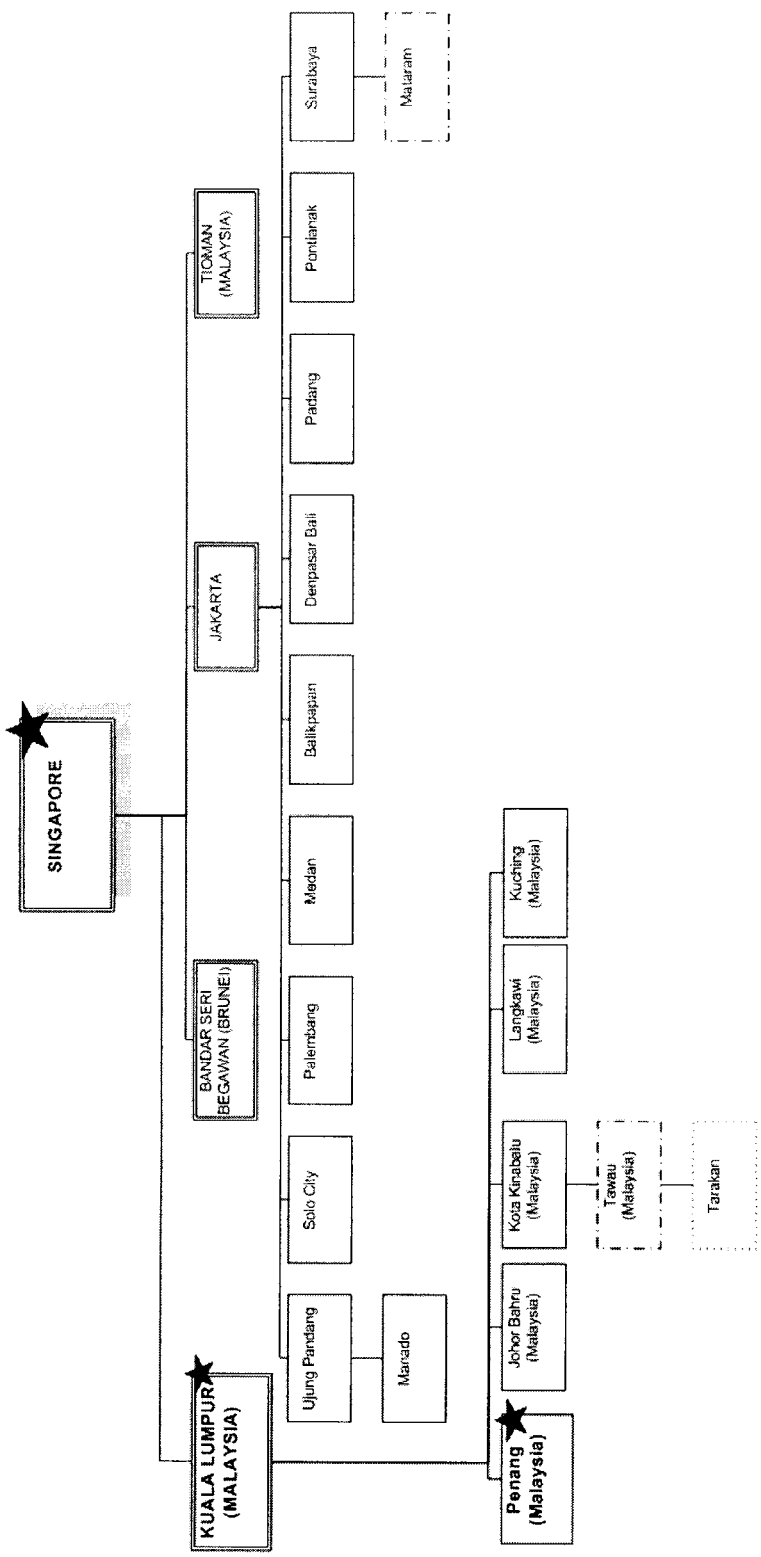
- FIGURE 20 -

| City Code | City Name | Country Name | # of Simulations with Importation | % of Total Simulations | Actual Observed Importation of SARS |
|---|---|---|---|---|---|
| TYO | Tokyo | Japan | 250 | 100% | Confirmed |
| TPE | Taipei | Chinese Taipei | 250 | 100% | Confirmed |
| KUL | Kuala Lumpur | Malaysia | 250 | 100% | Confirmed |
| MNL | Manila | Philippines | 250 | 100% | Confirmed |
| BKK | Bangkok | Thailand | 250 | 100% | Confirmed |
| SEL | Seoul | Korea Republic of | 250 | 100% | Probable |
| OSA | Osaka | Japan | 250 | 100% | Not Reported |
| SIN | Singapore | Singapore | 250 | 100% | Confirmed |
| LON | London (GB) | United Kingdom | 250 | 100% | Confirmed |
| KHH | Kaohsiung | Chinese Taipei | 249 | 99.6% | Confirmed |
| SYD | Sydney (AU) | Australia | 248 | 99.2% | Probable |
| FRA | Frankfurt | Germany | 245 | 98.0% | Confirmed |
| LAX | Los Angeles | USA | 245 | 98.0% | Confirmed |
| SFO | San Francisco | USA | 244 | 97.6% | Confirmed |
| YVR | Vancouver | Canada | 241 | 96.4% | Confirmed |
| PAR | Paris | France | 240 | 96.0% | Confirmed |
| JKT | Jakarta | Indonesia | 233 | 93.2% | Not Reported |
| FUK | Fukuoka | Japan | 228 | 91.2% | Not Reported |
| MEL | Melbourne (AU) | Australia | 227 | 90.8% | Confirmed |

- FIGURE 21 -

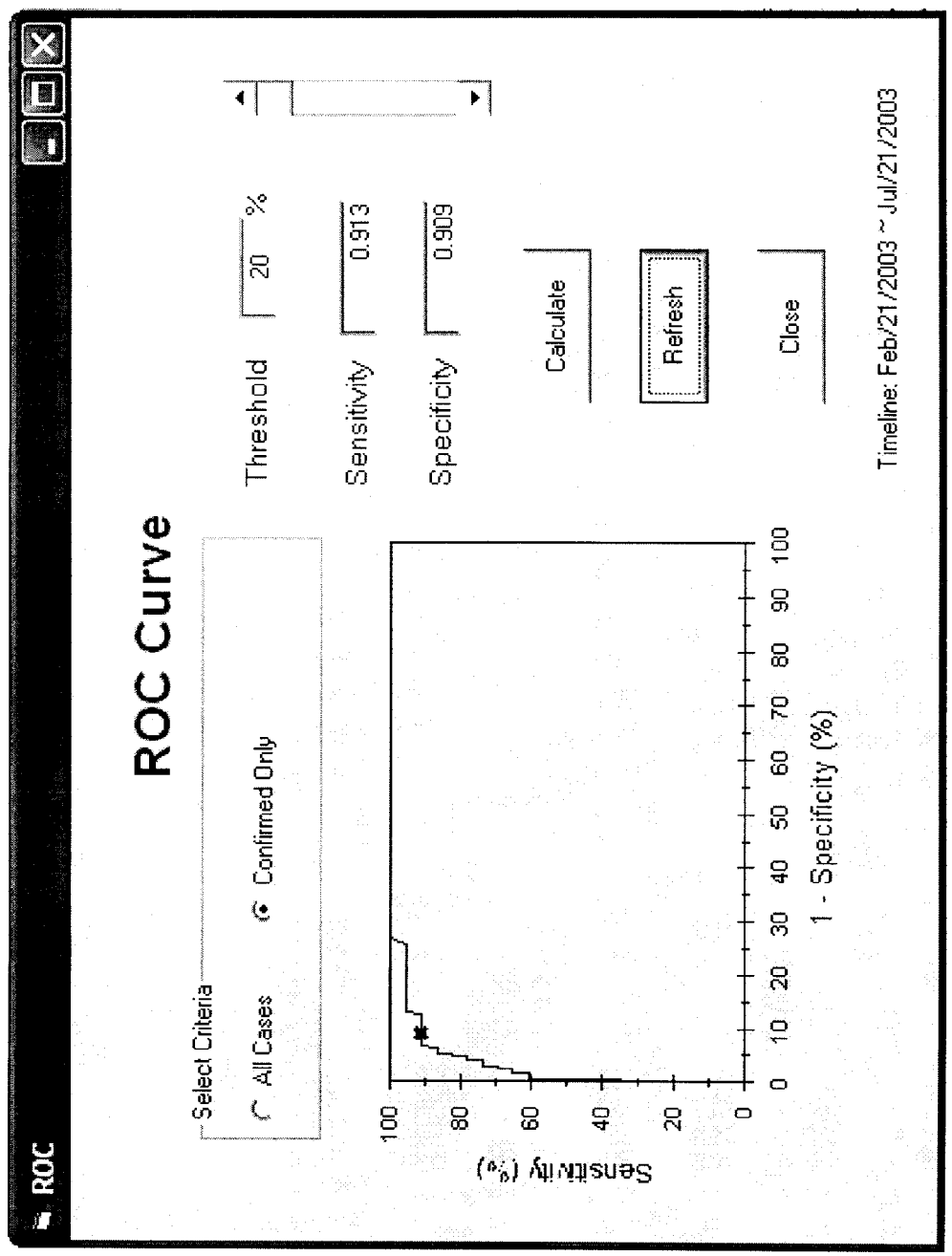
- FIGURE 22 -

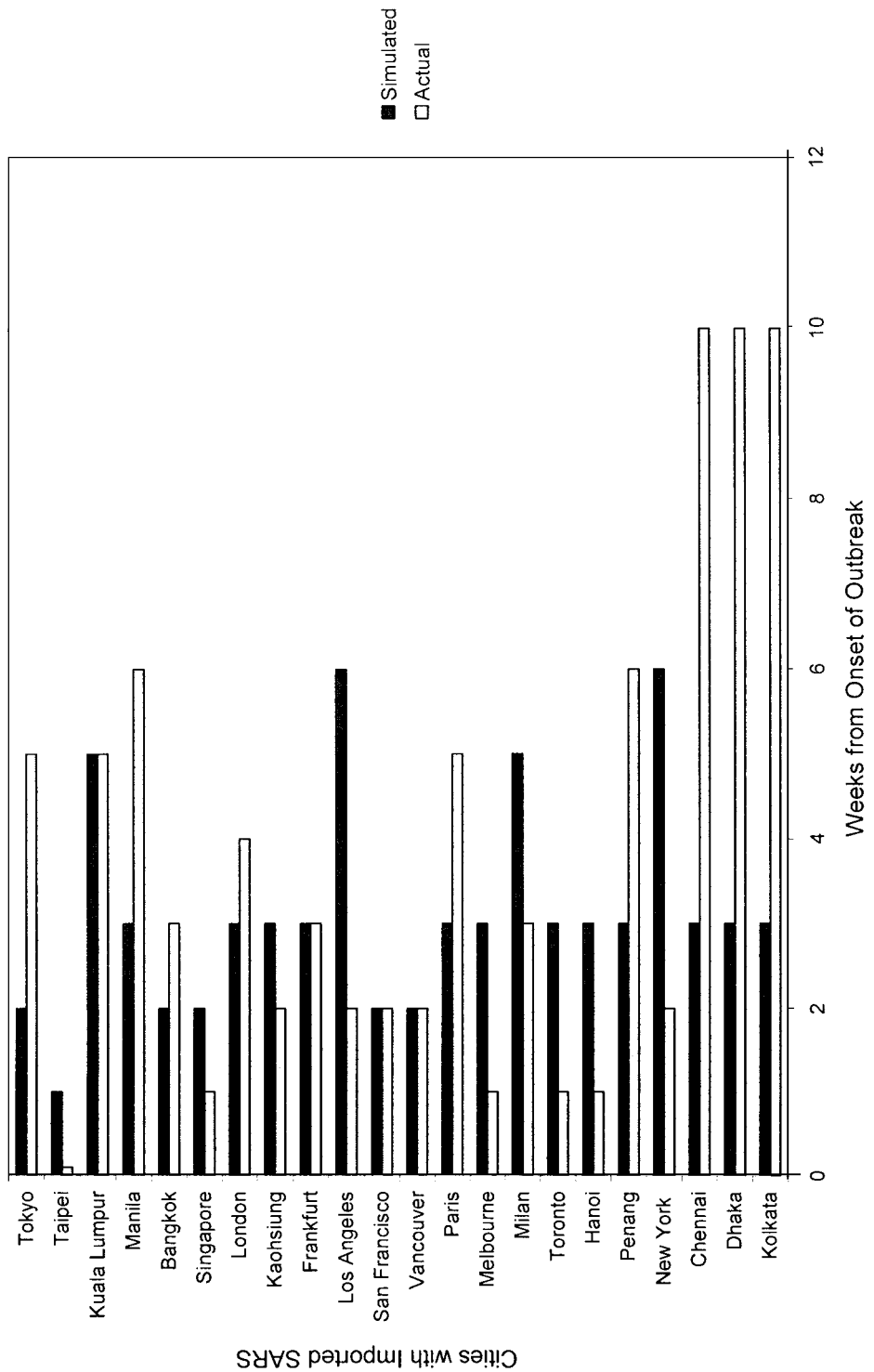
- FIGURE 23 -

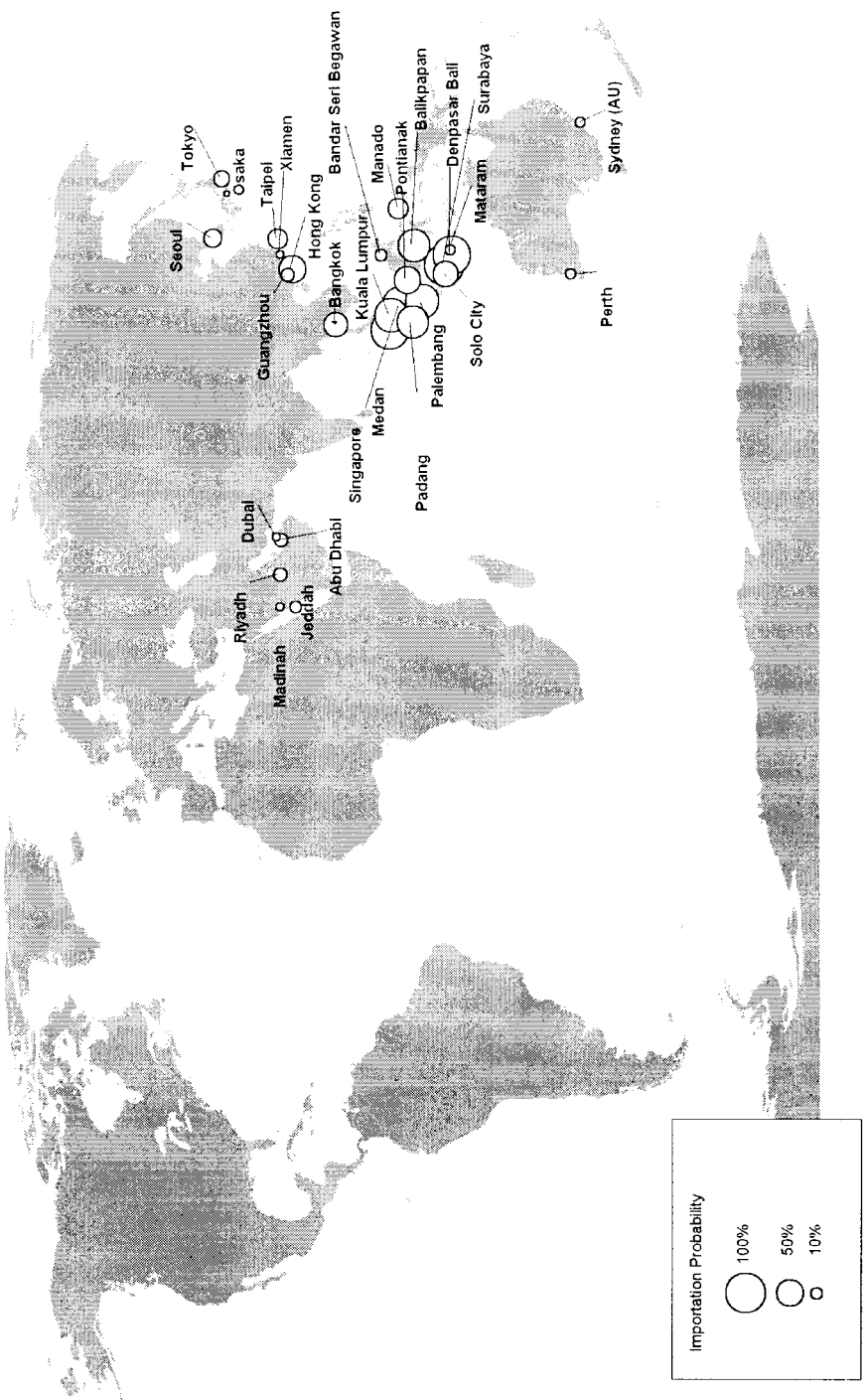
- FIGURE 24 -

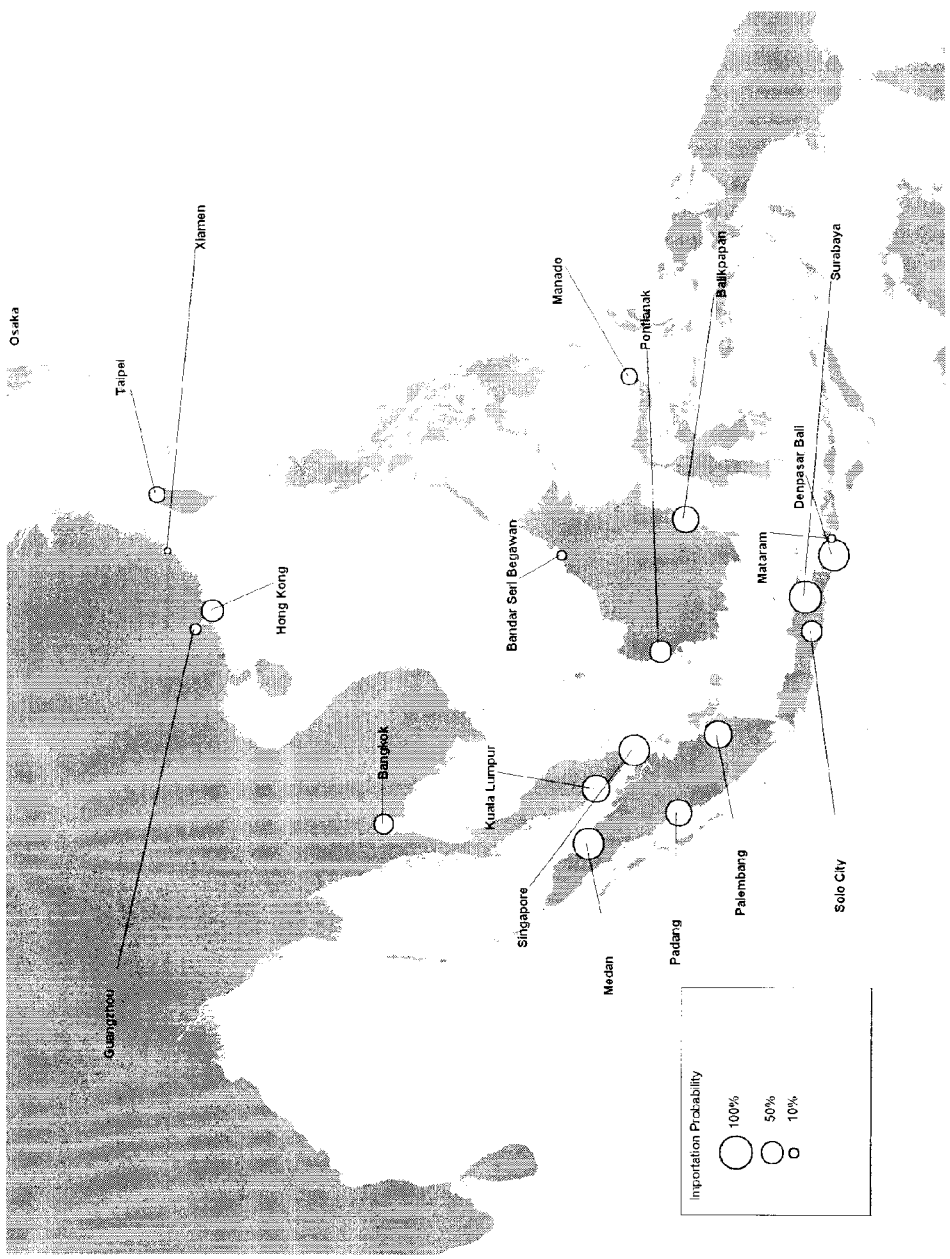
- FIGURE 24A -

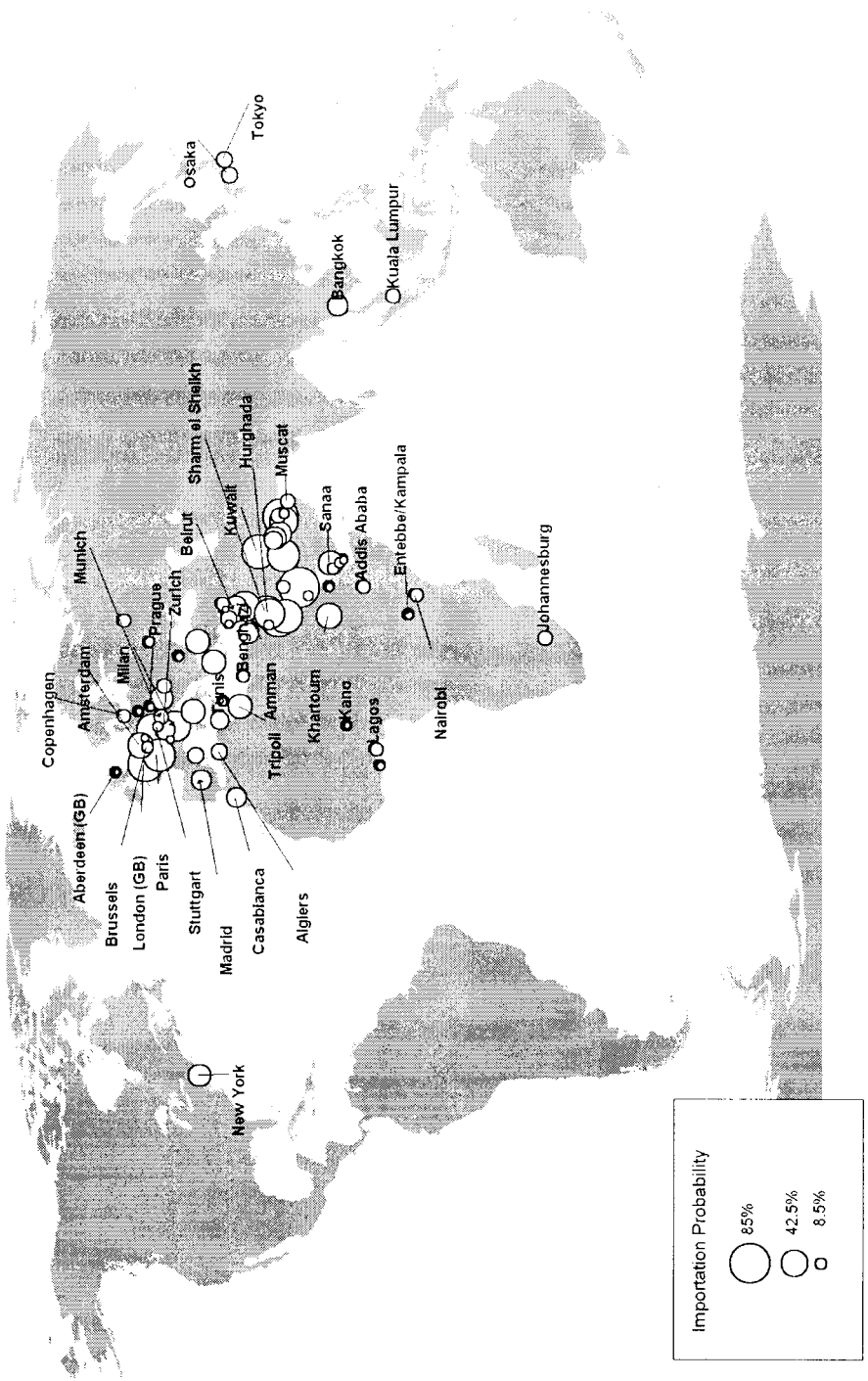
- FIGURE 25 -

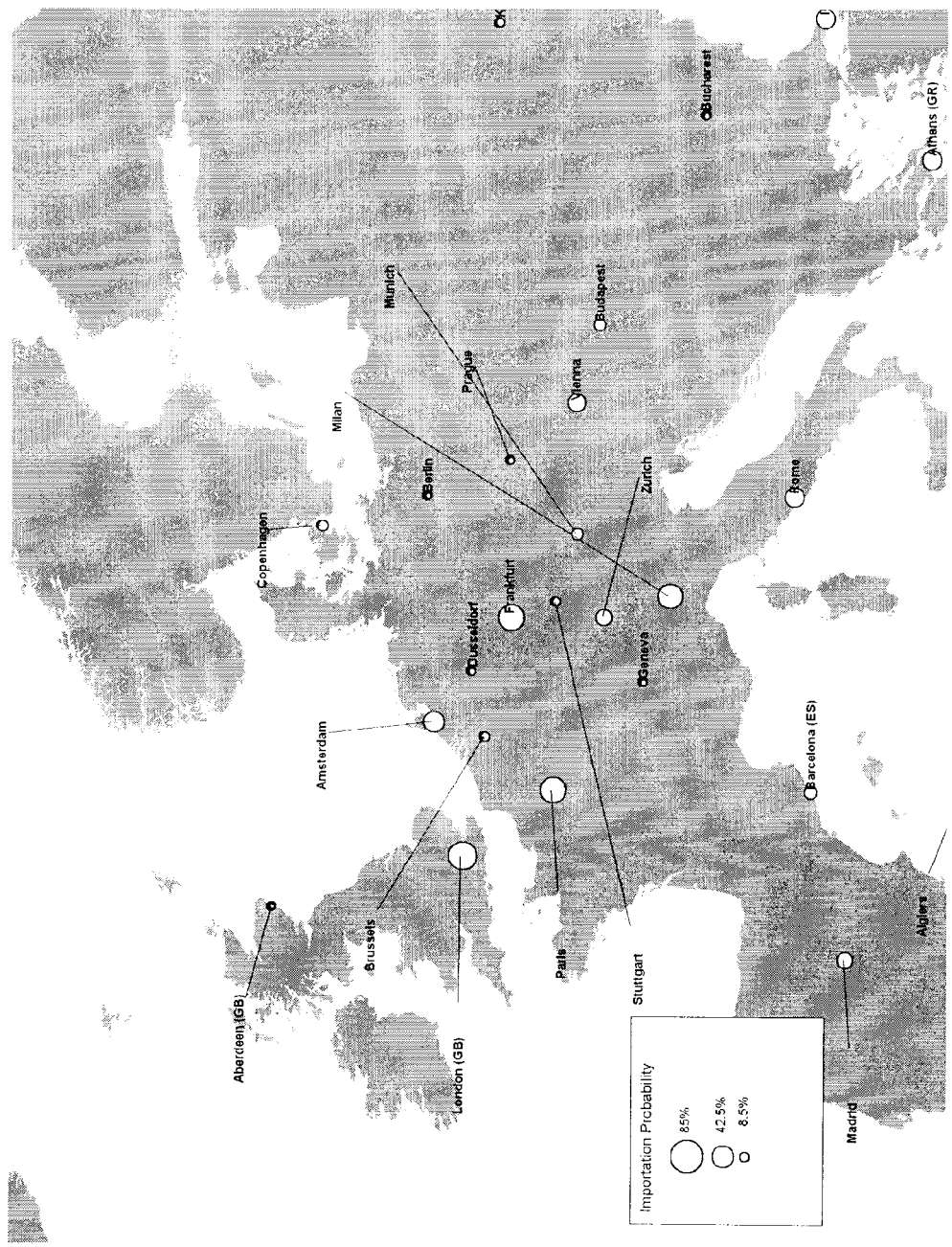
- FIGURE 25A -

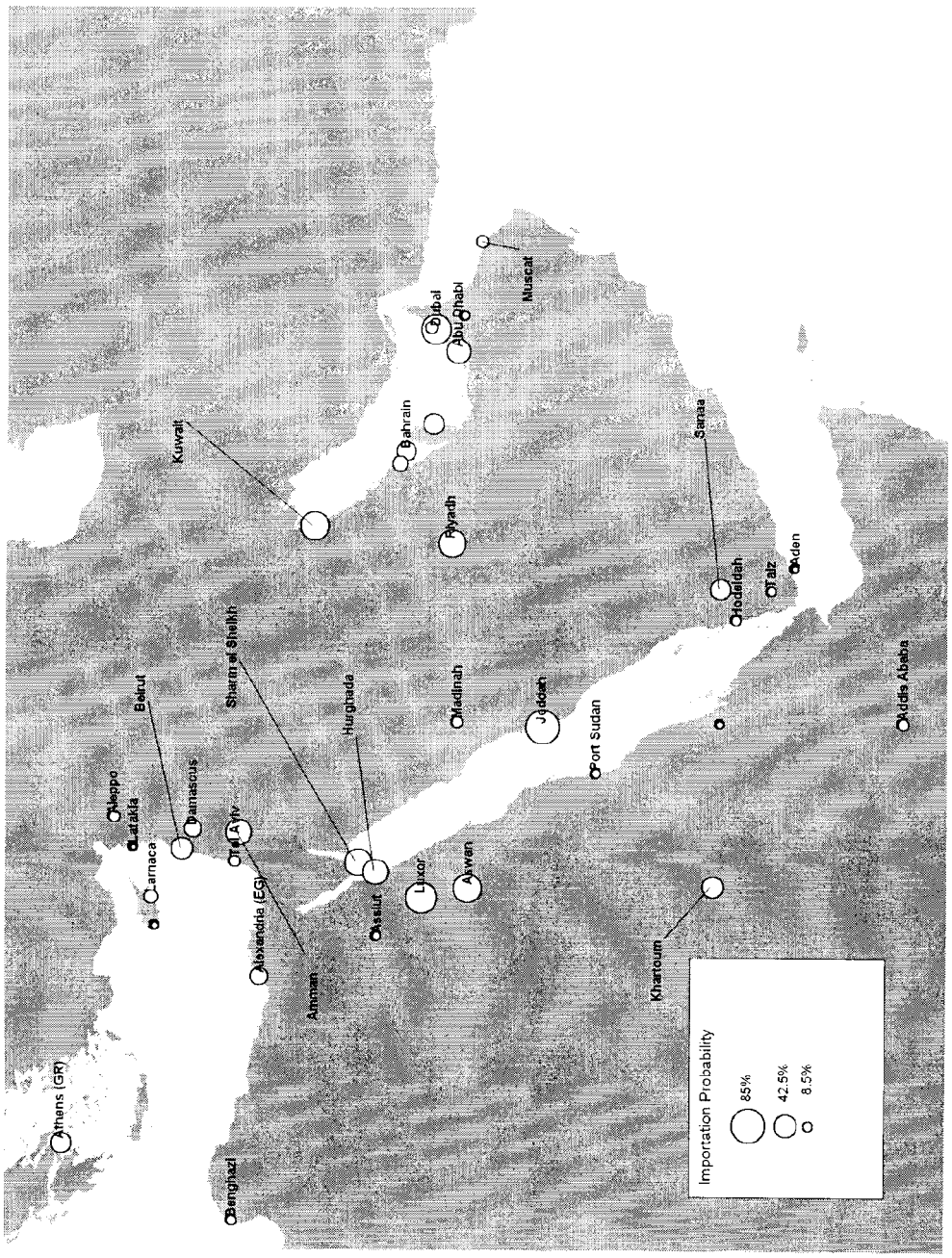

SYSTEM AND METHOD TO PREDICT THE GLOBAL SPREAD OF INFECTIOUS AGENTS VIA COMMERCIAL AIR TRAVEL

FIELD OF THE INVENTION

The present invention relates to the field of medicine and public health. Specifically, it involves predicting the spatial and temporal spread of human infectious agents via the worldwide airline transportation network.

BACKGROUND OF THE INVENTION

The relationship between human migration and the spread of infectious diseases has been well documented throughout human history. However, since the advent of intercontinental air travel in the 20th century, a massive, continuously expanding and evolving global airline transportation network has emerged to meet the world's surging demand for mobility. Concurrently, an explosion in global population has resulted in rising numbers of people traveling across greater distances in shorter and shorter time periods. Presently, the global airline transportation network carries more than two billion passengers per year. While the global airline transportation network has created a more interconnected world, it has also evolved into a major conduit for the spread of potentially dangerous infectious agents.

FIG. 1 demonstrates the evolution of global factors contributing to emergence and spread of infectious diseases. During the past century, global population growth has surged, reaching an estimated 6.7 billion people worldwide in 2008. Since the advent of intercontinental commercial aviation in the mid $20^{th}$ century, the time required for an individual to circumnavigate the globe has dropped precipitously, reaching less than 24 hours—shorter than the minimum incubation period for most human infectious diseases. Moreover, the phenomenon of global warming contributes to the expansion of ecological niches for important infectious disease vectors such as ticks and mosquitoes, which in turn is conducive to the emergence and reemergence of infectious diseases in human populations. Recognition of this "perfect storm" is growing, as documented in the 2007 World Health Report on Global Public Health Security in the $21^{st}$ century ISBN 978 92 4 156344 4. The report indicates that since the 1970s, new infectious disease threats have emerged at an unprecedented rate of one or more per year and that "Infectious diseases are now spreading geographically much faster than at any time in human history" [quote from Dr. Margaret Chan, Director General of the World Health Organization].

The emergence in 2003 of severe acute respiratory syndrome (SARS) and its subsequent dissemination via commercial aircraft to twenty-six countries on four continents provided irrefutable evidence that international and even intercontinental borders are highly permeable to the spread of infectious diseases. Post-SARS, confirmed human cases of avian H5N1 influenza across Asia and Africa have raised concerns that an influenza pandemic could be imminent. After the intentional spread of anthrax spores via the United States postal service in 2001, speculation over the intentional release of smallpox virus sparked additional fears of a pandemic. Whether originating from breaches at laboratories harbouring dangerous infectious pathogens, bioterrorism, or natural causes, outbreaks of emerging diseases with pandemic potential constitute a vital threat to the health and economic security of the entire international community.

Despite the role of commercial aviation as a major vehicle for the spread of emerging infectious diseases, knowledge of the global airline transportation network and its relationship to global security and public health remains extremely limited to date. Yet there is evidence to suggest that in today's world, the international and intercontinental spread of infectious diseases will occur predominantly via commercial air travel, and that the trajectories with which the disease will spread are, to a large extent, predictable. As proof of principle, a remarkably predictable relationship was identified between the structure of and flow of passengers on the global airline transportation network and the observed international spread of the SARS coronavirus in 2003. This association, observed during an outbreak that has been frequently dubbed a "pandemic dress rehearsal", inspired the development of further research converging expertise in medicine, infectious diseases, statistics and mathematics, networks, geography, and computer sciences. Consequently, an invention was needed to provide governments, businesses, and other organizations with the information necessary to fully appreciate their vulnerabilities in a highly interconnected and interdependent world. More importantly, a need was identified to rapidly generate evidence-based strategic plans to mitigate the risks associated with dangerous global infectious disease threats, and to do so in a manner that is uniquely tailored to the stated needs and global "footprint" of a given client at any specified point in time.

It is an object of this invention to partially or completely fulfill one or more of the above-mentioned needs.

SUMMARY OF THE INVENTION

The invention, referred to herein, solely for ease of reference, as DiaSPORA, assists entities such as cities, states, government agencies, public health organizations, corporations, and other groups protect their vital health and/or economic interests from global infectious disease threats. DiaSPORA acts to extract, process, and analyze large volumes of worldwide commercial aviation statistics and microdata for the intended purpose of characterizing human mobility across the world's cities. Applying this information, the invention predicts how, inside or outside an outbreak setting, an infectious agent is likely to disseminate via the global airline transportation network. The science behind the invention has its origins in epidemiological lessons learned during the worldwide outbreak of SARS, network analysis, and mathematical simulation modeling.

Additionally, DiaSPORA helps organizations strategically prepare for anticipated infectious disease threats before they occur, develop rapid strategic countermeasures to suspected or confirmed threats as they arise, and iteratively respond to suspected or confirmed outbreaks as they evolve and as new information about them becomes available. Although presently limited by the current speed in which commercial aviation data can be accessed, the invention possesses real-time forecasting capabilities and can respond to real-time data collection technology.

Operationally, DiaSPORA is designed to mitigate the risks associated with national or international infectious diseases threats stemming from natural causes (e.g. an influenza pandemic), bioterrorism (e.g. an intentional release of smallpox), laboratory accidents (e.g. a biosafety level 4 laboratory breach), or other unforeseen circumstances. Outbreaks may include those involving agents known to cause human infections (e.g. human influenza virus), agents with the potential to cause human infections (e.g. avian influenza virus), and/or agents that can survive on fomites (i.e. inanimate objects such as shoes or clothing) and be transported via commercial aviation (e.g. picornavirus causing hoof and mouth disease in animals). Infectious agents that are communicable and have substantial public health and/or economic consequences are those of greatest concern. DiaSPORA transforms empirical and simulation data into a set of evidence-based risk-mitigation strategies that are directed globally, locally, and/or at travel itself, and presented for consideration to decision-makers.

The invention, in one aspect, comprises a system for predicting transmission of an infectious agent via air travel, comprising: a) a database, the database containing air passenger travel data for air travel between origin cities and destination cities, the air passenger travel data including: frequency of flights from origin cities to destination cities, number of passengers traveling from origin cities to destination cities, number of direct non-stop flights from origin cities to destination cities, total passenger traffic for origin and destination cities, and corresponding date stamps for all air passenger travel data; b) a modeling engine operative to map the air passenger travel data with the infectious agent to determine the probability of infection of an individual destination city from an individual origin city via air travel; and c) a reporting engine operative to produce a probability of infection of the individual destination city from the individual origin city at a given time based on said map.

The invention, in another aspect, comprises a method of predicting the transmission of an infectious agent via air travel, comprising: a) retrieving air passenger travel data for air travel between origin cities and destination cities from a database, said air passenger travel data including: frequency of flights from origin cities to destination cities, number of passengers traveling from origin cities to destination cities, number of direct non-stop flights from origin cities to destination cities, total passenger traffic for origin and destination cities, and corresponding date stamps for all air passenger travel data; b) modeling probabilities for transmission of the infectious agent from an individual origin city to an individual destination city over a specific time period, the modeling based on the air passenger travel data; and c) generating a report of the probability of infection of the individual destination city from the individual origin city during the time period.

Other and further advantages and features of the invention will be apparent to those skilled in the art from the following detailed description thereof, taken in conjunction with the accompanying drawings.

BRIEF DESCRIPTION OF THE DRAWINGS

The invention will now be described in more detail, by way of example only, with reference to the accompanying drawings, in which like numbers refer to like elements, wherein:

FIG. 1: Global population size and mobility, 1850 to 2000

FIG. 2: Summary of the invention's primary components and processes

FIG. 3: Satellite images used to estimate population density in Egypt (FIG. 3A: left) and measure nighttime ambience of cities in northeastern United States and Canada (FIG. 3B: right) as a surrogate marker for economic development FIG. 4: Worldwide media reports pertaining to SARS and official World Health Organization travel advisories during the course of the 2003 outbreak FIG. 5: Geographic coordinates for all 1,061 commercial airports operating international flights worldwide in 2003

FIG. 6: International passenger volumes (i.e. arrivals and departures combined) for all 1,061 commercial airports worldwide, 2003

FIG. 7: International destinations accessible via direct non-stop flights departing Hong Kong (n=60), and corresponding passenger volume, 2003

FIG. 8: Confirmed international dissemination of SARS coronavirus to 23 cities using convalescent serology and/or polymerase chain reaction assay, 2003

FIG. 9: Intensity of confirmed SARS coronavirus importation to 23 cities using convalescent serology and/or polymerase chain reaction assay, 2003

FIG. 10: Probability of SARS importation to 960 cities with international airports by number of flights required to reach from Hong Kong International Airport, 2003

FIG. 11: Probability of SARS importation to 960 cities with international airports, by volume of international passenger arrivals from all destinations, 2003

FIG. 12: Passenger flows from Hong Kong International Airport into Taiwan and corresponding magnitude of SARS importation, 2003

FIG. 13: Kaplan-Meier analysis displaying timing of SARS importation to cities by presence or absence of direct non-stop flights departing from Hong Kong FIG. 14: DiaSPORA screenshot demonstrating major functions (left) and analytic customization by specified time (right)

FIG. 15: DiaSPORA screenshot demonstrating analytic customization by geographic location (Hong Kong) and direction of passenger flow (inbound)

FIG. 16: DiaSPORA screenshot displaying cities with direct non-stop flights arriving into Hong Kong in 2003, sorted by passenger volume FIG. 17: International locations with direct non-stop flights departing to Toronto (n=120), and corresponding passenger departure volume, 2003

FIG. 18: Four regional networks of cities within North America and the Caribbean islands in 2003, defined using principle components (factor) analysis FIG. 19: DiaSPORA screenshot displaying hierarchical structure of Hong Kong's (inbound) regional network of cities in 2003, defined using graph theory FIG. 20: Hierarchical structure of Singapore's regional network of cities in 2003, defined using graph theory, and cities with imported SARS FIG. 21: Spatial congruence between simulated SARS outbreak and observed SARS importation during 2003 worldwide outbreak FIG. 22: Receiver operating characteristics (ROC) curve displaying sensitivity and specificity of SARS simulations adopting selected thresholds FIG. 23: Temporal congruence between simulated SARS outbreak and observed SARS importation during 2003 worldwide outbreak FIG. 24: Results of simulated four-week outbreak of SARS originating from Jakarta, Indonesia on Jan. 1, 2006 and disseminating via commercial aviation FIG. 24A: Enlarged inset of Southeast Asia from FIG. 24

FIG. 25: Results of simulated four-week outbreak of SARS originating from Cairo, Egypt on Jan. 1, 2006 and disseminating via commercial aviation FIG. 25A: Enlarged inset of Western Europe from FIG. 25

FIG. 25B: Enlarged inset of Middle East and Northeast Africa from FIG. 25

DETAILED DESCRIPTION OF THE INVENTION

As used herein, an "infectious agent" or "agent" refers to a living or non-living entity such as a bacterium, virus, fungus, parasite, or prion that may result in active or latent infection in humans or other animal or plant species. For the purposes of this invention, attention is given to circumstances where infectious agents may be transported via commercial aviation within the human body or externally on its surface (i.e. on fomites or inanimate objects such as articles of clothing) and which carry potential health and/or economic consequences to human populations. Hereinafter, these circumstances are often referred to as "infectious disease threats".

The inventive system and method presented herein comprises, in a preferred embodiment, the components and processes shown in FIG. 2. The invention, referred to herein, solely for ease of reference, as DiaSPORA, contemplates partial or complete fulfillment of one or more of the following objectives:

Produce a system and method designed to integrate, organize and remotely access for analytic purposes, historical, contemporary and, where available, future data on the architecture of the entire global airline transportation network and the network's corresponding commercial aircraft and passenger flow dynamics. The system integrates worldwide commercial aviation data from multiple sources with worldwide data pertinent to the emergence and/or propagation of infectious agents of public health and/or economic significance. These data will include, but not be restricted to, information about infectious agents known to cause disease in humans, those with the potential to evolve and cause disease in humans, and those with the potential of being transported by humans via commercial air travel. Contextual information pertinent to the emergence and/or propagation of such agents can also be integrated and may include: i) population size, density, and demographics, ii) environmental conditions such as altitude, temperature, and humidity, iii) healthcare infrastructure and resources, iv) economic growth and development, and v) other miscellaneous factors.

Produce a system and method to rapidly and accurately define how the global airline transportation network is evolving with time, and how any given entity ("entity" hereafter refers to a commercial airport, city, state, country, regional authority, government, corporation, organization, or combination thereof) is interconnected within the global network at a selected point or period in time. Such information is derived through analysis of data described above and used to characterize the entity's vulnerability to imported infectious agents via commercial aviation.

Produce a system and method to rapidly conduct mathematical simulations of infectious disease outbreaks for the purposes of predicting the (spatiotemporal) spread of the agent via the global airline transportation network. The system and method facilitates a broad range of simulated conditions including those tailored, but not limited, to: i) characteristics of known infectious agents as well as those previously unrecognized (i.e. where characteristics such as the agent's mode(s) of transmission, basic reproduction number, incubation period etc. can be estimated); ii) geographic coordinate(s) where the infectious agent is suspected or confirmed to be present and/or propagating, and iii) geographic coordinate(s) to protect by preventing, disrupting, or delaying the importation of the agent via commercial aircraft.

Create a system and method to produce a framework for an entity to inspect the architecture of its global interconnectedness prior to the onset of an anticipated infectious disease threat and consequently comprehend its vulnerability to the importation of infectious agents via the global airline transportation network. With the use of empirical data, the value of potential strategies to mitigate the risks of importing potentially dangerous infectious agents via commercial air travel will be objectively evaluated.

Create a system and method to produce a framework for an entity to protect its health and/or economic interests by rapidly developing a strategic response plan designed to prevent, disrupt, or delay the importation of an infectious agent via commercial air travel amidst a new suspected or confirmed outbreak.

Create a system and method to produce a framework for an entity to protect its health and/or economic interests by rapidly developing iterative strategic response plans designed to prevent, disrupt, or delay the importation of an infectious agent via commercial air travel as new information pertaining to the outbreak becomes available.

Create a system and method to generate comprehensive reports tailored to the conditions surrounding an anticipated, suspected, or confirmed infectious disease threat and the declared self-interests of a specified entity. Reports are structured to evaluate strategies directed at different levels, including at the global level (i.e. those outside the entity's defined boundaries such as enhanced surveillance at targeted international locations), local level (i.e. those inside the entity's defined boundaries such as risk-appropriated health and human resource allocation), and travel itself (i.e. those in between the global and local levels such as travel restrictions).

Referring to FIG. 2, the primary components and processes involved in the invention are shown in abstract. In Step 1, use of the invention is triggered in the presence of an infectious disease threat caused by an agent capable of being carried internally within the human body (as latent or active infection) or externally on fomites (i.e. inanimate objects such as shoes or clothing) and consequently transported worldwide via commercial aviation. Infectious agents carrying potentially serious public health and/or economic consequences are those where the invention provides its greatest value. Threats may include outbreaks that are anticipated, suspected, or confirmed and which stem from natural causes (e.g. an influenza pandemic), bioterrorism (e.g. an intentional release of smallpox), laboratory accidents (i.e. a biosafety level 4 laboratory breach), or other unforeseen circumstances. Based upon the nature of the threat, operators of the invention are electively or emergently called into action.

In Step 2, operators of the invention access a database, developed specifically for this invention, which houses worldwide commercial aviation statistics and microdata in addition to other data pertinent to global infectious disease threats. During this step, microdata are extracted for processing and further analysis.

In Step 3, microdata are organized in a manner consistent with the intended response(s). These responses may include preparing for an anticipated threat that has not yet occurred, rapidly developing strategic countermeasures to a newly suspected or confirmed threat, and/or rapidly developing strategic countermeasures to an ongoing suspected or confirmed threat (e.g. outbreak) iteratively as it evolves and as new information becomes available.

In Step 4, large volumes of commercial aviation microdata and other pertinent data are analyzed through a series of automated algorithms. These analyses involve conducting i) network analyses that rigorously characterize connectivity and vulnerability of an entity to global infectious disease threats and ii) mathematical simulations that forecast how a specified infectious agent under defined conditions would likely disseminate worldwide via commercial air travel.

In Step 5, a comprehensive report is generated examining potential strategies aimed at mitigating the risks associated with an infectious disease threat of public health and/or economic significance.

Potential strategies for consideration by a client may include those directed at: i) the "global" level (i.e. at locations outside a potential client's defined boundaries), ii) the "local" level (i.e. at locations inside a potential client's defined boundaries), and iii) travel itself (i.e. at locations in between the global and local levels). A non-comprehensive list of potential clients include: i) major public health organizations (e.g. World Health Organization), ii) corporations or other members of the business community (e.g. insurance companies, multinational corporations), or iii) government agencies (e.g. national defense, public health agencies at federal, state/provincial, or municipal levels).

Based on the above-described general steps, the inventive system and method described herein comprises the following main components which are described in further detail below:

A Global Cities Database (GCD) housing historical, contemporary and future data pertaining to the global airline transportation network, the world's cities, and global infectious disease threats.

A software application known as DiaSPORA, designed to rapidly extract, process, analyze, and simulate the worldwide spread of infectious agents via the global airline transportation network.

A final output tailored to counter specific infectious disease threats and protect the declared interest(s) of potential clients in accordance with user-defined circumstances and conditions.

GCD: Worldwide Commercial Aviation Data

Aviation statistics and microdata are primarily derived from the following five organizations:
1. Airports Council International (ACI)
2. Official Airline Guide (OAG)
3. Marketing Information Data Tapes (MIDT)
4. International Airline Transportation Association (IATA)
5. International Civil Aviation Organization (ICAO)

Aviation statistics and microdata from the aforementioned sources are converged using IATA airport codes, which in turn are used to define the architecture of the global airline transportation network and characterize worldwide population mobility at a specified point or period in time. Inbound and outbound architecture and passenger flow dynamics are measured separately since flight routes between airport pairs are not always bidirectional, and may involve unidirectional flow around multi-point polygons. Passenger flow dynamics are also measured for daily, weekly, monthly, and seasonal variance to account for "natural" patterns of variability. At this time, the available data include historical, contemporary, and future data on flight schedules up to one year in advance. Data include information on scheduled movements of commercial aircraft and passenger seats, actual movements of commercial aircraft and passenger seats, and actual movements of passengers (i.e. distinguishing occupied from vacant seats). The majority of commercial aviation files also include information on passengers in transit (i.e. those simply connecting to another destination). All data include date stamps associated with the data, the date stamps including time stamps, if available. Data are available at the airport level thereby facilitating statistical calculations pertaining to any selected pair of commercial airports worldwide at a specified point or period in time. In GCD, data can be analyzed from the perspective of a commercial airport, municipality, airline, airline alliance (e.g. SkyTeam, OneWorld, Star Alliance), or a specific route between any pair of airports worldwide.

GCD: Population Demographics and Dynamics

Population demographics are typically obtained using census data. However, there are challenges in using national census data when conducting analyses at the global level. First, all countries worldwide do not perform censuses during the same year. For some countries where military conflicts are underway, security concerns may have precluded a national census for some time. Second, at the city-level, census data reflect areas where people reside but not necessarily where they work or spend a significant period of their time (e.g. few people live around commercial airports but many people "occupy" the space in and around commercial airports). Finally, the definitions of cities and their boundaries are highly variable making it difficult to measure city population in a consistent fashion. One solution to the above challenges entails the use of satellite data to estimate population size and density.

Referring to FIGS. 3A and 3B, they depict satellite images of (3A) population density in Egypt (left) and (3B) nighttime ambience of cities in the Northeastern United States and Canada (right). The images are used to derive estimates of population size and nighttime ambience (which is used in the invention as a surrogate marker for economic development) for a selected geographic area. These estimates come directly from the U.S. National Oceanic and Atmospheric Administration where the primary data are collected and analyzed and used as inputs in the invention's mathematical models.

GCD: Economic Development

Economic development may be related to conditions favouring the emergence of previously unrecognized infectious agents or the reemergence of known agents. International economic development data may be obtained using World Development Indicators published by the World Bank, although these data are only reported at the national level. There may be limitations to using such data, particularly for countries where resources are not homogeneously distributed (e.g. developing countries such as China and India). An alternative and potentially complementary approach to measuring economic development at the city level involves the use of satellite data. Specifically, the ambience or light intensity of cities when viewed from space at nighttime (as discussed above with reference to FIG. 3B) may be an important surrogate marker for economic development. The hypothesis for the use of this surrogate marker being that "brighter" cities are more developed and economically prosperous than those that are "darker".

GCD: Healthcare Infrastructure

The ability of a city to detect the presence of an infectious agent within its boundaries, prevent it from spreading locally, and/or prevent it from being exported to other cities may be associated with locally available healthcare infrastructure and human resources. Data of this kind (e.g. national estimates of the number of physicians and registered nurses, proportion of national gross domestic product allocated to public healthcare, etc.) can be obtained from the Health, Nutrition and Population statistical division of the World Bank. However, since these statistics are only reported at the national level, an assumption must be made that resources are allocated proportional to population size for cities within a given country.

GCD: Environmental Conditions

The characteristics and activity of virtually all infectious agents are influenced by environmental conditions such as temperature, humidity, and altitude. Such global data is obtained from a variety of environmental sources to identify locations where infectious agents might prosper and/or establish new ecological niches.

GCD: Human and non-Human Infectious Agents

While infectious disease outbreaks of varying scale are a common occurrence worldwide, GCD will focus its attention on global infectious disease threats that carry serious public health and/or economic repercussions. GCD will be updated on a frequent basis to incorporate the most current information available on anticipated, suspected, or confirmed global infectious disease threats worldwide (e.g. human infections resulting from H5N1 avian influenza) using a variety of reputable public and private sources.

GCD: Miscellaneous Data

Additional data sources can be added in the future to reflect new knowledge about specific infectious diseases, conditions favouring their emergence or reemergence, and/or factors associated with the local or global spread of such diseases.

By way of example, FIG. 4 is a depiction of the number of media reports about SARS published worldwide in English, French, Spanish, Chinese (traditional or simplified), or Japanese on any given day during the 2003 outbreak. These data were obtained from Factiva, a database with access to more than 10,000 media sources including newspapers, journals, magazines, news and radio transcripts from 152 countries in 22 different languages, including more than 120 continuously updated newswires. The figure also depicts the timing of major travel advisories issued by the World Health Organization. These data are used to examine associations between access to information via the global media, official travel advisories, and their intended or unintended effects on human travel behaviours worldwide. The lessons learned are integrated into the inventive sytem and method to better anticipate how travel behaviours might be influenced by infectious disease threats and force adjustments to the data and/or the model.

Invention Proof of Principle

The invention is established upon a principle that the spread of infectious agents via commercial aviation is determined by the architecture of the global airline transportation network and the associated movements of passengers on it. Through rigorous study of the 2003 worldwide outbreak of SARS (often referred to as a "pandemic dress rehearsal"), support of this principle has been demonstrated in the manner described below.

Step 1: Obtain worldwide commercial aviation statistics and microdata during the course of the international SARS outbreak These microdata were obtained from the Official Airline Guide (www.oag.com) and facilitated an analysis of the architecture of the entire global airline transportation network and the movement of scheduled passenger seats between virtually every commercial airport worldwide in 2003. Since the overwhelming majority of SARS cases that breached an international border did so via commercial aircraft departing from Hong Kong's International Airport, the analysis was centred upon the connectedness of Hong Kong with the rest of the world.

Referring to FIG. 5, it identifies the geographic coordinates of all 1,061 commercial airports operating international flights worldwide in 2003.

Referring to FIG. 6, it displays global variance in international passenger flows (arrivals and departures combined) in 2003, represented as peaks in a three dimensional representation of the world. While too complex to be presented graphically, the software developed for this invention is designed to rapidly extract, process, and analyze passenger arrival and/or departure data for any airport-pair at any specified point or period in time.

Referring to FIG. 7, it represents a tailored analysis, quantifying international passenger volume to all sixty cities receiving direct non-stop flights from Hong Kong in 2003. This "outbound" analysis was conducted to identify potential locations at heightened risk of SARS importation during the 2003 outbreak.

Step 2: Collect Detailed Information on the International Spread of SARS

The World Health Organization (WHO) has published national summary data on imported probable cases of SARS as of Dec. 31, 2003. These data, however, do not include information at the municipal level or information pertaining to the mode of diagnosis for each of the 142 imported cases that crossed an international border during the outbreak. For research purposes, the following data were collected from laboratories and public health agencies around the globe for each imported probable case of SARS:

1. Port of departure and port of arrival, including intermediate stops;
2. Date of departure and date of arrival to aforementioned ports;
3. Mode of travel (i.e. air, land, sea);
4. Method of SARS diagnosis—epidemiological case definition, polymerase chain reaction (PCR) assay, and/or convalescent serology (i.e. presence of antibodies to the SARS coronavirus at least 28 days after the onset of illness); and
5. Number of imported SARS cases and method of diagnosis for each.

Referring to FIG. 8, this depiction of the international trajectories of all confirmed SARS cases during the 2003 outbreak demonstrates that more than 90% of all cases were directly or indirectly translocated from Hong Kong's International Airport. The international spread of SARS via air travel from Hohhot (China) to Ulaanbaatar (Mongolia) and Guangzhou (China) to Kuala Lumpur (Malaysia) are shown separately since the arrival of SARS into Hohhot and Guangzhou occurred by land (from Guangdong province in mainland China) and as such, had no direct or indirect connections with Hong Kong by air.

Referring to FIG. 9, this map depicts the intensity of confirmed, imported SARS cases worldwide in 2003. These observations have been used to study the "dose-response effect" between the architecture of the global airline transportation network, its passenger flows, and the observed intensity of SARS importation.

Step 3: Measure Statistical Associations Between Characteristics of the Global Airline Transportation Network and the Observed Spread of Confirmed (or Confirmed and Probable) Cases of SARS.

Referring to FIG. 10, it demonstrates that cities with direct non-stop flights arriving from Hong Kong International Airport during the SARS outbreak had more than a forty-fold increased risk of confirmed SARS importation relative to cities requiring one flight connection to reach. Not a single city worldwide which was (as of 2003) two or more flight connections away from Hong Kong received an imported (confirmed or probable) SARS case at any time during the course of the outbreak. These findings strongly suggest that cities with direct non-stop flights to the epicentre of an infectious disease outbreak carry a substantially heightened risk of disease importation.

Referring to FIG. 11, it demonstrates that cities with the highest international passenger arrival volumes worldwide had the greatest risk of SARS importation. For example, cities receiving more than 10 million international passenger arrivals in 2003 had more than a one hundred fold increase in risk of importation than cities receiving fewer than 1 million international passenger arrivals.

Referring to FIG. 12, it graphically displays the "dose-response" relationship between passengers departing Hong Kong's International Airport and arriving into Taiwan with the associated intensity of SARS importation into Taiwan. Flight connections between mainland China and Taiwan and are somewhat unique in that they almost exclusively pass through Hong Kong (Macau is alternatively used to a much lesser degree). This figure is consistent with the underlying hypothesis that the intensity of SARS importation (or importation of other infectious agents) will parallel passenger flows along an air traffic artery, in this case, air traffic between Hong Kong and Taiwan's two international airports located in Taipei and Kaohsiung.

Referring to FIG. 13, it displays a Kaplan-Meier plot depicting the time to SARS importation among cities worldwide by their connectedness to Hong Kong through air travel. The figure demonstrates that the timing of SARS importation was strongly influenced by the connectedness of cities to Hong Kong by air. Specifically, cities with direct non-stop flights arriving from Hong Kong received imported SARS cases at a substantially faster rate than cities without such non-stop connections. Not shown on this figure is timing of a WHO travel advisory advocating the restriction of all non-essential travel to Hong Kong and Guangdong province in mainland China less than one week before the "flattening" of the curve at day 42. While this is an association, it remains unclear if the advisory was causally related to the change in the course of the outbreak or was a random and unrelated association. Further research into the event will be required to explore the intended and/or unintended effects of the advisory on actual travel behaviours.

Step 4: Develop Models to Simulate and Predict the Spread of SARS

A deterministic (modified classical SEIR) mathematical simulation model using ordinary differential equations (ODE) was developed to forecast the spread of SARS in 2003. Concurrently, a parallel stochastic (Markovian) model was developed to examine the distribution of potential "realizations" of the worldwide outbreak of SARS. By comparing results from both simulation models with the actual spread of SARS (as identified in Step 2) the models can be validated. The mathematical model section described below (under the Deterministic Model and Stochastic Model sub-headings) provide a more in-depth description of the models, the steps involved in developing them, and the degree of concordance between a mathematically simulated SARS outbreak and events actually observed during the outbreak of 2003.

DiaSPORA: General Description

The software prototype known as DiaSPORA was developed in Microsoft Visual Basic 6.0 with migration currently underway into Visual Basic.NET (VB.NET). This transition is being performed to facilitate secure, tiered, remote access and operation of the invention via the Internet since its use may be required urgently and without notice. A virtual platform also permits operators of the invention to operate it regardless of where they are located (which may have considerable importance in the midst of an infectious disease threat) and facilitates guest access for key decision makers and clients. The newly developed DiaSPORA software will be designed to integrate other existing software applications such as SAS® (statistical analysis), ESRI ArcGIS and Pitney Bowes MapInfo (GIS and spatial analysis), Berkeley Madonna (mathematical analysis), and Microsoft Office (presentation and communication of results) relevant to operating the invention. Through the use of efficient processing algorithms, automation of analytic processes and advancements in computer technology, DiaSPORA will become increasingly efficient at producing the highest quality output in shorter and shorter periods of time. Future software packages may be added into DiaSPORA as needed.

Referring to FIG. 14, it depicts a screenshot from an introductory screen of DiaSPORA, demonstrating its ability to process and analyze microdata in accordance with a user-defined point or period in time. Data available for processing and analysis from GCD, as described above, include historic and contemporary commercial aviation statistics and microdata, in addition to flight schedules microdata as far as one year into the future. The time frame selected for this hypothetical analysis is Jan. 1 to Dec. 31, 2003.

Referring to FIG. 15, it also depicts a screenshot from a geographic selection screen of DiaSPORA, demonstrating its ability to process and analyze microdata in accordance with a user-defined geographic location and specified direction of flow. The analysis can be tailored to any entity such as airport, city, state, or other organization. Although not shown in this figure, DiaSPORA is also capable of constructing an analytic unit that is not geographically contiguous (e.g. a multinational corporation with business centres across distant cities and countries). DiaSPORA also allows the user to select a direction for the analysis since the inbound and outbound architecture (and passenger flows) on the global airline transportation network are not identical. In this figure, the selected analysis examines the inbound architecture and flow of international passengers arriving into Hong Kong.

DiaSPORA: Network Analysis

For any user-defined circumstance and set of conditions, DiaSPORA performs a rigorous network analysis to define the precise architecture in which a given entity is connected within the global airline transportation network.

First, direct connectivity is analyzed in terms of the minimum number of stops required to travel between a given city-pair. As identified during the worldwide SARS outbreak of 2003, a city's vulnerability to an external infectious disease threat appears to be inversely related to its "distance", as measured by the number of flights needed to translocate that "distance". Thus, a city can quickly identify if it is directly (i.e. non-stop connections exist) or indirectly (flight connections required) in the "line of fire" of an infectious disease threat.

Referring to FIG. 16, DiaSPORA performs an analysis of direct connectivity, displaying inbound flows via non-stop flights into Hong Kong from all international locations worldwide for the selected time frame of Jan. 1 to Dec. 31, 2003. The data, which can be exported for further analysis, demonstrate that over 4.3 million passengers arrived into Hong Kong from Taipei in 2003, accounting for 18.1% of all international inbound volume. Half of all international inbound traffic into Hong Kong was accounted for by six cities (i.e. Taipei, Bangkok, Singapore, Tokyo, Manila, and Beijing). Data shown in this figure include total inbound passenger volume, percentage of total inbound passenger volume, and cumulative percentage of inbound volume by way of example, however numerous other network parameters pertaining to connectivity, centrality, and communality are additionally generated.

FIG. 17, by way of example, displays a similar analysis of all international inbound traffic into the city of Toronto via non-stop flights from 120 destinations worldwide in 2003. Through a combination of tabular formats and graphical representations, information about a direct connectivity is efficiently communicated to clients or users of the invention.

Second, indirect connectivity is analyzed using two complementary methodologies: principle components (factor) analysis and applied graph theory. These approaches are used to define the scope and hierarchical structure of "networks", each of which encompasses of a collection of highly interconnected cities. For example, a city may not have nonstop flights connecting it directly to the epicentre of an infectious disease outbreak, but member cities within its own network may have such links. An examination of the scope and hierarchical structure of the network in which a particular entity or city resides sheds valuable light on how vulnerable its "neighbours" might be to a particular infectious disease threat.

Referring to FIG. 18, this map of North America identifies using principle components (factor) analysis, four major networks of cities. While the networks have been somewhat arbitrarily referred to as US East, US West, Canada East and Canada West networks, they in fact are defined entirely independent of geopolitical boundaries or considerations. For example, the city of Toronto has "stronger" ties to the US Eastern network than it does to other cities within Canada. Furthermore, cities within Mexico and the Caribbean islands are so extensively linked to the United States and parts of Canada that they share a common network.

Referring to FIG. 19, the screenshot displays a list of cities belonging to Hong Kong's (inbound) city network. The figure indicates in the far right ("network") column that Hong Kong is the hierarchical "head" of global network 21 (55 networks have been identified worldwide in 2003). While the first number indicates the network ID number, subsequent numbers describe its hierarchical structure. In this example, Bangkok is nested below Hong Kong, while Chiang Rai, Koh Samui, and Vientiane are parallel to one another and nested below Bangkok. Furthermore, Utapao is nested below Koh Samui and Luang Prabang below Vientiane. Using graph theory to examine a segment of the airline transportation network provides important visual cues and statistical data about how vulnerable or sequestered a given location is within the scope of the broader global network. Although not shown in this figure, the architecture of the global airline transportation network is multi-dimensional and can be described at various levels in DiaSPORA (shown as low-level, middle-level, and high-level).

FIG. 20 is derived using the same process described for FIG. 17 but is displayed graphically. This figure shows the hierarchical architecture of the network in which Singapore resided in 2003. Furthermore, cities with stars represent locations where SARS was confirmed to have been imported by air. Although not demonstrated in this specific example, the overwhelming majority of SARS cases crossing an international border via commercial air travel landed in cities at the top of their regional network, sparing the more sequestered locations below.

DiaSPORA: Mathematical Simulations

Two types of mathematical models have been developed—the first derived adopting a deterministic framework, while the second uses a stochastic framework.

Deterministic Model: This type of model was derived from a classical SEIR (Susceptible, Exposed, Infectious, and Removed) framework and adapted for the purposes of this invention. The ordinary differential equation (ODE) below is applied to model the transmission dynamics of an infectious agent within a given city, denoted by subscript i:

$$\frac{d}{dt}S_i = \prod_i + v_i R_i - \beta_i \frac{S_i I_i}{N_i} - d_i S_i$$

$$\frac{d}{dt}E_i = \beta_i \frac{S_i I_i}{N_i} - (d_i + \varepsilon_i)E_i$$

$$\frac{d}{dt}I_i = \varepsilon_i E_i - (d_i + \gamma_i)I_i$$

$$\frac{d}{dt}R_i = \gamma_i I_i - (d_i + v_i)R_i$$

where $1/\varepsilon_i$ represents the mean duration of the infectious agent's latency period and $1/\gamma_i$ represents the mean duration of infection before removal by death or recovery.

The SEIR model was subsequently modified to account for commercial air travel between cities and is shown below (adaptations to the original equation are circled):

$$\frac{d}{dt}S_i = \Pi_i + v_i R_i - \beta_i \frac{S_i I_i}{N_i} - d_i S_i + \sum_{j=1}^{n} m_{ji}^S S_j - \sum_{j=1}^{n} m_{ij}^S S_i$$

$$\frac{d}{dt}E_i = \beta_i \frac{S_i I_i}{N_i} - (d_i + \varepsilon_i)E_i + \sum_{j=1}^{n} m_{ji}^E E_j - \sum_{j=1}^{n} m_{ij}^E E_i$$

$$\frac{d}{dt}I_i = \varepsilon_i E_i - (d_i + \gamma_i)I_i + \sum_{j=1}^{n} m_{ji}^I I_j - \sum_{j=1}^{n} m_{ij}^I I_i$$

$$\frac{d}{dt}R_i = \gamma_i I_i - (d_i + v_i)R_i + \sum_{j=1}^{n} m_{ji}^R R_j - \sum_{j=1}^{n} m_{ij}^R R_i$$

$$m_{ij} = \frac{\text{Number of passengers flying from airport } i \text{ to airport } j}{\text{Total number of passengers flying out of airport } i}$$

It is anticipated that the analytic horizon of simulations conducted by the invention will generally be in the order of weeks (with iterative simulations being performed as new information pertaining to the infectious disease threat and/or commercial aviation data become available). Consequently, the above equation can be simplified to remove the susceptible compartment (i.e. which approximates the general population living within a city and will experience negligible change within a short-range simulation) and the removed compartment (i.e. since the total number of persons who are removed due to immunity or death will be negligible relative to the total population across all compartments during a short-range simulation). Thus, the equation can be reduced to its final simplified form, which significantly eases computer processing demands and decreases simulation time.

$$\frac{d}{dt}E_i = \beta_i I_i - \varepsilon_i E_i + \sum_{j=1}^{n} m_{ji}^E E_j - \sum_{j=1}^{n} m_{ij}^E E_i$$

$$\frac{d}{dt}I_i = \varepsilon_i E_i - \gamma_i I_i + \sum_{j=1}^{n} m_{ji}^I I_j - \sum_{j=1}^{n} m_{ij}^I I_i.$$

Stochastic Model:

This type of model was developed to examine the distribution of possible realizations stemming from a single event (i.e. a specific infectious disease threat). Apart from the use of Markov processes, the model is conceptually similar to the simplified two-compartment, deterministic ordinary differential equation (ODE) model above. By evaluating the outcomes of each simulation individually, it enables an estimation of the probability of importation for any given city and is well adapted for spatiotemporal forecasting applications. When significantly large numbers of simulations are performed, the "average" value observed in the stochastic model tends to approximate the "calculated" value derived from the deterministic model.

The process $$X(t):=(E_1(t),I_1(t),\ldots,E_n(t),I_n(t)), t\geq 0$$

is defined as the Markov process that verifies the following assumptions. For all j∈I we assume:

1. In a time interval of length h, a susceptible is infected in airport j, i.e., $$(e_1,i_1,\ldots,e_j,i_j,\ldots,e_n,i_n)\to(e_1,i_1,\ldots,e_j+1,i_j,\ldots,e_n,i_n)$$

with probability $$p(h)=\beta_j i_j h+o(h)$$

2. In a time interval of length h, recovery of an infected individual in airport j, i.e., $$(e_1,i_1,\ldots,e_j,i_j,\ldots,e_n,i_n)\to(e_1,i_1,\ldots,e_j,i_j-1,\ldots,e_n,i_n)$$

with probability $$p(h)=\gamma_j i_j h+o(h)$$

3. In a time interval of length h, an exposed individual develops the disease in airport j, i.e., $$(e_1,i_1,\ldots,e_j,i_j,\ldots,e_n,i_n)\to(e_1,i_1,\ldots,e_j-1,i_j+1,\ldots,e_n,i_n)$$

with probability $$p(h)=\varepsilon_j e_j h+o(h)$$

4. In a time interval of length h, an exposed individual in airport j is transferred to airport k (with k≠j) i.e., $$(e_1,i_1,\ldots,e_j,i_j,\ldots,e_k,i_k,\ldots,e_n,i_n)\to(e_1,i_1,\ldots,e_j-1,i_j+1,i_k,\ldots,e_n,i_n)$$

with probability $$p(h)=m_{jk}^E e_j h+o(h)$$

for all k∈$\mathcal{T}$.

5. In a time interval of length h, an infected individual in airport j is transferred to airport k (with k≠j) i.e., $$(e_1,i_1,\ldots,e_j,i_j,\ldots,e_k,i_k,\ldots,e_n,i_n)\to(e_1,i_1,\ldots,e_j,i_j-1,\ldots,e_k,i_k+1,\ldots,e_n,i_n)$$

with probability $$p(h)=m_{jk}^I i_j h+o(h)$$

for all k∈$\mathcal{T}$.

6. In a time interval of length h, there is no change in the system, i.e., $$(e_1,i_1,\ldots,e_j,i_j,\ldots,e_n,i_n)\to(e_1,i_1,\ldots,e_j,i_j,\ldots,e_n,i_n)$$

with probability $$p(h)=1-fh+o(h)$$

where $$f:=\sum_{j=1}^{n}(\beta_j i_j+\gamma_j i_j+\varepsilon_j e_j)+\sum_{j,k=1,k\neq j}^{n}(m_{jk}^E e_j+m_{jk}^I e_j)$$

The expected values in the model $\overline{E}_i:=\mathbb{E}(E_i(t))$ and $\overline{I}_i:=\mathbb{E}(I_i(t))$ verify the deterministic model.

FIG. 21 represents output from a simulated outbreak of SARS originating in Hong Kong on Feb. 21, 2003 and continuing over a 22 week period (designed to parallel conditions surrounding the actual outbreak in 2003). Results from the invention's stochastic simulation model (running a total of 250 simulations) identify cities predicted to be at greatest risk of importation (i.e. with a simulated probability exceeding 90%). The column furthest to the right shows what was actually observed during the SARS outbreak. Of the simulated 19 highest risk cities worldwide, 16 had either probable or confirmed SARS importation.

FIG. 22 summarizes through a receiver operating characteristic (ROC) curve, the stochastic model's discrimination and calibration specifications with respect to the worldwide outbreak of SARS. When comparing results from the 250 conducted simulations with actual confirmed SARS importations, the model had 91.3% sensitivity and 90.9% specificity. Given that these simulations are stochastic (and represent different possible realizations of a single event), results across simulations vary to some extent. Nonetheless, in numerous large-scale spatial simulations of SARS, the invention has uniformly exceeded a 90% sensitivity and 90% specificity threshold, with an area under the curve (AUC) consistently ranging between 0.90 and 0.95.

FIG. 23 depicts the temporal component of the invention's spatiotemporal simulation capabilities. Specifically, the figure demonstrates congruence between the median week of simulated SARS importation with the actual week of SARS importation observed during the outbreak. Use of more refined passenger flow data (if available) during an outbreak (i.e. ideally over short time horizons such as a single day) would likely further enhance temporal precision. Nonetheless, 61% and 83% of simulated SARS importations (during the above simulation) landed within two and four weeks of the observed week of SARS importation respectively.

FIG. 24 and FIG. 25 represent results from hypothetical, simulated SARS outbreaks originating in Jakarta, Indonesia and Cairo, Egypt respectively on Jan. 1, 2006 with results observed until Jan. 31, 2006. The probability of importation is depicted by the sizes of the circles overlying cities. For these figures, simulation parameters from the previous SARS model remained unchanged with modification only to the outbreak epicentre. The two figures demonstrate how differently an infectious outbreak could unfold from different points of origin worldwide.

Mathematical models in DiaSPORA can be modified to reflect different pathogen characteristics such as basic reproduction number, incubation period, and mode of transmission. Local population factors and dynamics can also be tailored to actual local conditions. Thus, by accessing the wealth of data in GCD, DiaSPORA can simulate the dispersion of different infectious agents from any city with a commercial airport worldwide with very short notice and deliver results within the span of hours.

OUTPUT: Potential Scenarios

By way of examples, a few scenarios involving potential infectious disease threats are described below to demonstrate how the invention might be used under real-world circumstances.

Hypothetical Scenario 1:

After suffering massive and ongoing economic damages from the local outbreak of SARS in 2003, the city of Toronto is looking to develop a comprehensive preventive strategy to mitigate its risks and vulnerabilities to global infectious disease threats. One component of that strategy entails an assessment of how Toronto is interconnected within the global community of cities and what possible strategies should be considered to protect its vital health and economic interests.

Hypothetical Response 1:

As an initial step, passenger microdata are extracted from GCD over a five year window (i.e. preceding four years in addition to future flight schedules data going one year into the future). All analyses described below are performed to identify time trends.

To assess direct connectivity, GCD microdata are analyzed to examine inbound flights and passenger arrivals from all cities with commercial airports worldwide, sorted by the number of stops required to reach Toronto and the volume of arriving international passengers.

To assess indirect connectivity, principle components (factor) analysis is used to identify the network of cities in which Toronto resides, while applied graph theory is used to define the hierarchical structure of the network. These analyses are conducted without consideration to geopolitical borders.

A list of global cities to which Toronto is most connected, directly and indirectly, is then evaluated for anticipated, suspected, or confirmed infectious disease threats. For example, cities located within or near an H5N1 avian influenza outbreak zone affecting poultry and/or humans would be considered to pose a heightened risk (i.e. for the possible onset of an influenza pandemic). Likewise, cities in which biosafety level 4 laboratories exist would also be considered locations of elevated risk. Using the above framework, a list of high risk cities would be generated and ranked in terms of their ability to rapidly detect and control an infectious disease threat, should one emerge. This ability would be estimated by quantifying the scope of health and human resources locally available using contemporary Health, Nutrition and Population statistical data from the World Bank. Thus, the definition of a high-risk cities would be derived as a composite of interconnectedness with Toronto, local risk for the emergence of an infectious disease threat, and local ability to detect and respond to a threat should one emerge.

A short list of Toronto's "highest-risk" cities would then be evaluated through mathematical simulations. Considering each of these locations as a potential epicentre under defined global and local conditions, an outbreak would be evaluated for its many possible simulated realizations. However, greatest attention would be paid to importation events with the highest probability. Strategic countermeasures to prevent, disrupt, and/or delay the risk of anticipated infectious disease threats would be proposed at the international level (e.g. heightened surveillance for infectious diseases, international investment in detection and control capabilities), local level (health and human resource allocation, investment in local surge capacity) and/or at travel itself (e.g. consideration for travel restrictions, heightened border screening).

Hypothetical Scenario 2:

A terrorist organization has announced the release of an undisclosed but highly communicable and lethal infectious agent at London's Heathrow airport 24 hours ago. During investigations to detect the presence of dangerous infectious pathogens at Heathrow airport, cities around the world have been placed on heightened alert by the World Health Organization and advised to watch carefully for signs of a local infectious disease outbreak.

Hypothetical Response 2:

This rapid response scenario would involve the swift extraction of flight schedules microdata from GCD at (and around) the declared time of the intentional release. Since actual passenger data from 24 hours earlier may not be available, counts of scheduled passenger seats (and possibly counts of scheduled passengers with purchased tickets if available) would be accessed. Scheduled passenger seat data would be modified by applying load factor estimates (i.e. the proportion of passenger seats occupied by passengers).

Like Hypothetical Scenario 1, all cities worldwide with commercial airports would be sorted by the number of stops away from London's Heathrow Airport (this analysis can be initiated at the airport level since the aggregation of data from multiple airports to the city level would be unnecessary) and counts of passenger (seat) volume.

Simulations involving the spread of this unverified and unidentified infectious agent out of Heathrow airport would be conducted and examined by the relative probabilities of importation to different cities around the globe. For this kind of simulation analysis, characteristics of the infectious agent could be estimated using a best or worst case scenario, presumed based on intelligence or other information, or ignored entirely with simulations halting when the infectious agent first "lands" in another city (i.e. local transmission within the "receiving" population would be ignored). Furthermore, all analyses would be tailored to the precise number of scheduled passenger seats (and/or estimated passengers occupying those seats) that departed Heathrow airport between the declared time of intentional release and subsequent announcement of the release. This calculation could in fact be calculated with down to the minute precision (assuming flights departed on time as scheduled). Consequently, cities on the "receiving" end of flights from Heathrow could then undertake appropriate measures to respond locally, in proportion to the estimated (simulated) degree of risk involved. Further use of the invention would presumably occur if intentional release of the infectious agent was verified and strategic control measures were sought to further disrupt or delay its spread via commercial air travel.

A somewhat similar scenario to the one described as Scenario 2 might entail an accidental or intentional laboratory breach at a biosafety level 3 or 4 laboratory harbouring dangerous infectious pathogens.

Hypothetical Scenario 3:

A large multinational corporation with operations in 7 cities around the globe is renewing its organization's insurance contract. The insurer raises concerns that several key operations in the company's organizational structure are located in Indonesia and Vietnam, areas where outbreaks of H5N1 involving humans have been ongoing and where it is feared an influenza pandemic may emerge. The insurer directly questions the corporation's insurability and suggests that a substantial increase in the cost of insurance may be in order unless these risks are mitigated. In response, the corporation pursues a rigorous analysis of its vulnerability to local and global infectious disease threats, with the intention of creating strategic operational redundancies and diversifying its vital operations to areas of the world that are more "sequestered" and carry a lower predicted risk. By creating a strategy to maintain business continuity at the global level, the corporation seeks to identify measures to protect its economic interests.

Hypothetical Response 3:

This scenario would be conducted in a similar fashion to Scenario 1, with exception to the manner in which the "entity" of interest is defined. For this analysis, the entity would be comprised of locations where the corporation maintains its headquarters and vital operations (i.e. 7 different cities in different countries). Although more complex than a single location, the corporation's direct and indirect connectivity can still be determined in the same manner as Scenario 1. Furthermore, sub-group analyses involving the most vital locations and operations could be considered and simulations tailored to a number of "most-likely" scenarios. Analyses could also be performed to coincide with peak business activity during a particular season or time of year. Analyses would subsequently be conducted on a scheduled (or as needed) basis to account for corporate expansion or restructuring and/or evolution of the global airline transportation network with time.

This concludes the description of a presently preferred embodiment of the invention. The foregoing description has been presented for the purpose of illustration and is not intended to be exhaustive or to limit the invention to the precise form disclosed. It is intended the scope of the invention be limited not by this description but by the claims that follow.

What is claimed is:

1. A system for predicting transmission of an infectious agent via air travel, comprising:
   a) a database, said database containing air passenger travel data for air travel between origin cities and destination cities, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   b) a modeling engine operative to determine probability of infection of an individual destination city from an individual origin city via air travel by mapping said air passenger travel data with the probability of emergence, propagation and infection for said infectious agent and producing one or more maps of times and locations for dissemination of said infectious agent; and
   c) a reporting engine operative to produce a probability report for an infection outbreak in said individual destination city from said individual origin city over a fixed time period based on said maps produced by said modeling engine.

2. The system of claim 1, wherein said database is updated in real-time.

3. The system of claim 1, wherein said reporting engine uses maps produced over different time periods to further produce a report of the likelihood of said infectious agent entering said destination city over a period of time.

4. The system of claim 1, further including a planning engine operative to combine local, national, and international level infectious disease response data with said maps produce a response plan based on said probability report and a selected level of response.

5. A system for predicting transmission of an infectious agent via air travel, comprising:
   a) a database, said database containing air passenger travel data for air travel between origin cities and destination cities, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   b) a modeling engine operative to determine probability of infection of said destination cities from an individual origin city via air travel by mapping said air passenger travel data with the probability of emergence, propagation and infection for said infectious agent and producing one or more maps of times and locations for dissemination of said infectious agent; and
   c) a reporting engine operative to produce a probability report for an infection outbreak in said destination cities from said individual origin city over a fixed time period based on said maps produced by said modeling engine.

6. The system of claim 5, wherein said database is updated in real-time.

7. The system of claim 6, wherein said reporting engine further produces a report of the likelihood of said infectious agent entering each said destination city over a period of time.

8. A system for predicting transmission of an infectious agent via air travel, comprising:
   a) a database, said database containing air passenger travel data for air travel between origin cities and destination cities, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   b) a modeling engine operative to map said air passenger travel data with said infectious agent to determine probability of infection of an individual destination city from said origin cities via air travel; and
   c) a reporting engine operative to produce a probability of infection of said individual destination city from said origin cities at a given time based on said map.

9. The system of claim 8, wherein said database is updated in real-time.

10. The system of claim 8, wherein said reporting engine uses maps produced over different time periods to further produce a report of the likelihood of said infectious agent entering said destination city over a period of time.

11. A system for predicting transmission of an infectious agent via air travel, comprising:
   a) a database, said database containing air passenger travel data for air travel between origin cities and destination cities, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data, with information in said database updated in real time;
   b) a modeling engine operative to determine probability of infection of an individual destination city from an individual origin city via air travel by iteratively mapping said air passenger travel data with the probability of emergence, propagation and infection for said infectious agent and producing one or more maps of times and locations for dissemination of said infectious agent; and
   c) a reporting engine operative to produce a probability report for an infection outbreak in said individual destination city from said individual origin city at the present time based on said maps produced by said modeling engine.

12. The system of claim 11, wherein said reporting engine uses maps produced over different time periods to further produce a report of the likelihood of said infectious agent entering said destination city over a period of time.

13. A method of predicting the transmission of an infectious agent via air travel, comprising:
   a) retrieving air passenger travel data for air travel between origin cities and destination cities from a database, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   b) modeling probabilities for transmission of said infectious agent from an individual origin city to an individual destination city over a specific time period via a modeling engine executing on a computer system, said modeling based on mapping said air passenger travel data with the probability of emergence, propagation and infection for said infectious agent and producing one or more maps of times and locations for dissemination of said infectious agent; and
   c) generating a report via a reporting engine executing on said computer system of the probability of infection outbreak in said individual destination city from said individual origin city during said specific time period based on said maps produced by said modeling step.

14. The method of claim 13, wherein said air passenger travel data is updated in real-time.

15. The method of claim 13, wherein said generating step uses maps produced over different time periods to generate a report of the likelihood of said infectious agent entering said destination city over a period of time.

16. The method of claim 13, further including steps of selecting a level of response to the infectious agent and producing a response plan by combining local, national, and international level infectious disease response data with said maps and the selected level of response.

17. A method of predicting the transmission of an infectious agent via air travel, comprising:
   a) retrieving air passenger travel data for air travel between origin cities and destination cities from a database, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   b) selecting an origin city;
   c) selecting a destination city;
   d) modeling probabilities via a modeling engine executing on a computer system for transmission of said infectious agent from said selected origin city to said selected destination city over a specific time period, said modeling based on mapping said air passenger travel data with the probability of emergence, propagation and infection for said infectious agent and producing one or more maps of times and locations for dissemination of said infectious agent; and
   e) generating a report via a reporting engine executing on said computer system of the probability of infection outbreak in said selected destination city from said selected origin city during said time period based on said maps produced by said modeling step.

18. The method of claim 17, wherein said air passenger travel data is updated in real-time.

19. The method of claim 17, wherein said generating step uses maps produced over different time periods to generate a report of the likelihood of said infectious agent entering said destination city over a period of time.

20. A method of predicting the transmission of an infectious agent via air travel, comprising:
   a) retrieving air passenger travel data for air travel between origin cities and destination cities from a database, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   b) selecting an origin city;
   c) selecting one or more destination cities;
   d) modeling probabilities for transmission of said infectious agent from said selected origin city to said selected destination cities over a specific time period via a modeling engine executing on a computer system, said modeling based on mapping said air passenger travel data with the probability of emergence, propagation and infection for said infectious agent and producing one or more maps of times and locations for dissemination of said infectious agent; and
   e) generating a report via a reporting engine executing on said computer system of the probability of infection outbreak in said selected destination cities from said selected origin city during said time period based on said maps produced by said modeling step.

21. The method of claim 20, wherein said air passenger travel data is updated in real-time.

22. The method of claim 20, wherein said generating step uses maps produced over different time periods to generate a report of the likelihood of said infectious agent entering each said destination city over a period of time.

23. A method of predicting the transmission of an infectious agent via air travel, comprising:
   a) retrieving air passenger travel data for air travel between origin cities and destination cities from a database, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamps for all said air passenger travel data;
   a) selecting one or more origin cities;
   b) selecting a destination city;
   d) modeling probabilities for transmission of said infectious agent from said selected origin cities to said selected destination city over a specific time period via a modeling engine executing on a computer system, said modeling based on mapping said air passenger travel data with the probability of emergence, propagation and infection for said infectious agent and producing one or more maps of times and locations for dissemination of said infectious agent; and e) generating a report via a reporting engine executing on said computer system of the probability of infection outbreak in said selected destination city from said selected origin cities during said time period based on said maps produced by said modeling step.

24. The method of claim 23, wherein said air passenger travel data is updated in real-time.

25. The method of claim 23, wherein said generating step uses maps produced over different time periods to generate a report of the likelihood of said infectious agent entering said destination city over a period of time.

26. A method of predicting the transmission of an infectious agent via air travel, comprising:
   a) retrieving current air passenger travel data for air travel between origin cities and destination cities from a database, said air passenger travel data including: frequency of flights from said origin cities to said destination cities, number of passengers traveling from said origin cities to said destination cities, number of direct non-stop flights from said origin cities to said destination cities, total passenger traffic for said origin and said destination cities, and corresponding date stamp for all said air passenger travel data;
   b) modeling current probabilities via a modeling engine executing on a computer system for transmission of said infectious agent from an individual origin city to an individual destination city, said modeling based on mapping said air passenger travel data with the probability of emergence, propagation and infection for said infectious agent and producing one or more maps of times and locations for dissemination of said infectious agent; and
   c) generating reports via a reporting engine executing on said computer system of the current probability of infection outbreak in said individual destination city from said individual origin city by iterative performance of said retrieval step and modeling step using updated data from said retrieval step.

27. The method of claim 26, wherein said generating step uses maps produced over different time periods to generate a report of the likelihood of said infectious agent entering said destination city over a period of time.

* * * * *